United States Patent
Botha et al.

(10) Patent No.: US 11,278,870 B2
(45) Date of Patent: Mar. 22, 2022

(54) COBALT-CONTAINING CATALYST COMPOSITION

(71) Applicant: Sasol South Africa Limited, Johannesburg (ZA)

(72) Inventors: Jan Mattheus Botha, Sasolburg (ZA); Denzil James Moodley, Vanderbijlpark (ZA); Jana Heloise Potgieter, Vaalpark (ZA); Hendrik Van Rensburg, Fife (GB); Jan Van De Loosdrecht, Sasolburg (ZA); Prabashini Moodley, Vanderbijlpark (ZA)

(73) Assignee: Sasol South Africa Limited, Johannesburg (ZA)

( * ) Notice: Subject to any disclaimer, the term of this patent is extended or adjusted under 35 U.S.C. 154(b) by 470 days.

(21) Appl. No.: 16/319,674

(22) PCT Filed: Jun. 22, 2017

(86) PCT No.: PCT/IB2017/053723
§ 371 (c)(1),
(2) Date: Jan. 22, 2019

(87) PCT Pub. No.: WO2018/029548
PCT Pub. Date: Feb. 15, 2018

(65) Prior Publication Data
US 2021/0213428 A1    Jul. 15, 2021

(30) Foreign Application Priority Data

Aug. 11, 2016   (ZA) ................................ 2016/05529

(51) Int. Cl.
*B01J 23/75*        (2006.01)
*B01J 23/889*       (2006.01)
(Continued)

(52) U.S. Cl.
CPC ........... *B01J 23/75* (2013.01); *B01J 23/8892* (2013.01); *B01J 31/32* (2013.01); *B01J 31/38* (2013.01);
(Continued)

(58) Field of Classification Search
None
See application file for complete search history.

(56) References Cited

U.S. PATENT DOCUMENTS

| | | | |
|---|---|---|---|
| 2012/0071571 | A1 | 3/2012 | Abbas et al. |
| 2014/0045953 | A1 | 2/2014 | Daly et al. |

(Continued)

FOREIGN PATENT DOCUMENTS

| | | |
|---|---|---|
| CN | 101203304 A | 6/2008 |
| CN | 103071481 A | 5/2013 |

(Continued)

OTHER PUBLICATIONS

Declaration under 37 C.F.R. 1.132 from related U.S. Appl. No. 15/546,864, filed Aug. 23, 2019 (Year: 2019).*

(Continued)

*Primary Examiner* — Colin W. Slifka
(74) *Attorney, Agent, or Firm* — Crowell & Moring LLP

(57) ABSTRACT

The present invention relates to catalysts, more particularly to a cobalt-containing catalyst composition. The present invention further relates to a process for preparing a cobalt-containing catalyst precursor, a process for preparing a cobalt-containing catalyst, and a hydrocarbon synthesis process wherein such a catalyst is used. According to a first aspect of the invention, there is provided a cobalt-containing catalyst composition comprising cobalt and/or a cobalt compound supported on and/or in a silica ($SiO_2$) catalyst support wherein the average pore diameter of the catalyst support is more than 20 nm but less than 50 nm; the catalyst compo- (Continued)

sition also including a titanium compound on and/or in the catalyst support, and a manganese compound on and/or in the catalyst support.

13 Claims, 8 Drawing Sheets

(51) Int. Cl.
    *B01J 31/32*     (2006.01)
    *B01J 31/38*     (2006.01)
    *B01J 35/10*     (2006.01)
    *C07C 2/10*     (2006.01)
    *C10G 2/00*     (2006.01)

(52) U.S. Cl.
    CPC ............. *B01J 35/1061* (2013.01); *C07C 2/10* (2013.01); *C10G 2/332* (2013.01); *C07C 2521/08* (2013.01); *C07C 2523/75* (2013.01)

(56) References Cited

U.S. PATENT DOCUMENTS

| | | |
|---|---|---|
| 2014/0088206 A1 | 3/2014 | Daly et al. |
| 2016/0074837 A1 | 3/2016 | Espinoza et al. |

FOREIGN PATENT DOCUMENTS

| | | | |
|---|---|---|---|
| CN | 103201030 A | 7/2013 | |
| CN | 103635256 A | 3/2014 | |
| CN | 103998132 A | 8/2014 | |
| CN | 105772107 | 7/2016 | |
| EP | 0966415 B1 * | 4/2002 | ........... C07C 1/0435 |
| JP | 2010-023022 A | 2/2010 | |
| JP | 2010-520043 A | 6/2010 | |
| JP | 2015-528747 A | 10/2015 | |
| WO | 2013088290 A1 | 6/2013 | |
| WO | 2014020507 A2 | 2/2014 | |
| WO | 2016135577 A1 | 9/2016 | |

OTHER PUBLICATIONS

International Search Report dated Oct. 16, 2017 for International Application No. PCT/IB2017/053723.
Chinese Application No. 201780040671.2 First Office Action (English translation).
Chinese Application No. 201780040671.2 Supplementary Search.
Japanese Application No. 2018-569061 dated Jun. 8, 2021 Decision to Grant Patent (English translation).
Japanese Application No. 2018-569061 dated Dec. 18, 2020 (English translation).
European Patent Application No. 17746183.7 Communication dated Mar. 23, 2020.
Canadian Patent Application No. 3,028,590 Examiners Requisition dated Apr. 16, 2021.

* cited by examiner

COBALT-CONTAINING CATALYST COMPOSITION

CROSS-REFERENCE TO RELATED APPLICATIONS

This application is a National Stage application of International Application No. PCT/IB2017/053723, filed Jun. 22, 2017. This application also claims priority under 35 U.S.C. § 119 to South African Patent Application No. 2016/05529, filed Aug. 11, 2016.

TECHNICAL FIELD

The present invention relates to catalysts, more particularly to a cobalt-containing catalyst composition. The present invention further relates to a process for preparing a cobalt-containing catalyst precursor, a process for preparing a cobalt-containing catalyst, and a hydrocarbon synthesis process wherein such a catalyst is used.

BACKGROUND ART

Hydrocarbon synthesis from synthesis gas (syngas) containing hydrogen and carbon monoxide in the presence of a Fischer-Tropsch (FT) synthesis catalyst is commonly known as FT synthesis. During the FT synthesis, the syngas is contacted with the FT synthesis catalyst under FT synthesis conditions to produce the hydrocarbons. One type of catalyst which is often used in low temperature FT (LTFT) synthesis comprises an active catalyst component such as Co supported on and/or in a catalyst support such as alumina, silica, titania, magnesia or the like, and the hydrocarbons produced are usually in the form of a waxy hydrocarbon product.

It is known that during FT synthesis the activity of catalysts, such as Co supported on a support, usually decreases over time (that is, the catalyst deactivates), with the result that less syngas is converted into hydrocarbons. This characteristic of a catalyst that its activity may decrease over time during hydrocarbon synthesis is referred to as the activity stability of the catalyst.

As stated above, a lack of activity stability of a catalyst has the effect that the catalyst deactivates over time and less hydrocarbons are then produced. To counter this effect, the temperature of the FT synthesis process may be increased to make up for the loss of activity of the catalyst. However, an increased reaction temperature has the disadvantage that more unwanted methane is formed during the FT synthesis. Other costly measurements such as increased catalyst loading, catalyst rejuvenation or catalyst reactivation may also be taken to recover the hydrocarbon production.

It is known in the art that many different components such as modifiers, dopants and promoters may be introduced into catalysts in order to improve certain aspects of the catalyst, such as improved hydrothermal stability, improved reducibility of the active component, improved activity of the catalyst, improved product selectivity of the catalyst and improved activity stability of the catalyst during FT synthesis. A long list of such components is known to be suitable for the purposes set out above, for example Si, Ti, Zr, Cu, Zn, Ba, Co, Ni, La, W, Na, K, Ca, Sn, Cr, Fe, Li, Tl, Mg, Sr, Ga, Sb, V, Hf, Th, Ce, Ge, U, Nb, Ta, Mn, Pt, Pd, Re and Ru. It has now been found that if Ti and Mn in combination are included in a cobalt-containing catalyst with a silica catalyst support wherein the average pore diameter of the catalyst support is more than 20 nm but less than 50 nm, unexpected advantages are obtained.

WO 2014020507; WO 9961550; Applied Catalysis A: General, 419-420 (2012) 148-155; WO 2008104793; WO 2012107718; AU2013203123; US 20120252665 A1; Fuel Processing Technology, 89 (2008) 455-459 and Catalysis Today, 197 (2012) 18-23 disclose the inclusion of Ti in catalysts.

The inclusion of Mn in catalysts is disclosed in Journal of Catalysis, 246 (2007) 91-99; Journal of Physical Chemistry B, 110 (2006), 8626-8639; EP 0966415 A1; U.S. Pat. No. 6,333,294 B1; US 20020010221 A1; Fuel Processing Technology, 90 (2009) 901-908; Journal of Catalysis, 288 (2012) 104-114; Journal of Catalysis, 237 (2006) 152-161; US 20080132589; US20080064769A1; US20100099780A1 and US20040127352 A1.

The inclusion of both Ti and Mn on a silica support is disclosed in PCT/IB2016/050745 which document has not been published at the time of the priority date of this application. PCT/IB2016/050745 is silent about the average pore diameter of more than 20 nm but less than 50 nm for silica supports.

Most surprisingly, it has now been found that when a supported cobalt catalyst, with a silica catalyst support wherein the average pore diameter of the catalyst support is more than 20 nm but less than 50 nm, includes both titanium and manganese, the activity and/or activity stability and/or C5+ productivity of the catalyst and/or lower methane selectivity of the catalyst and/or the attrition resistance of the support is improved during hydrocarbon synthesis wherein syngas is contacted with the catalyst. This is illustrated by the inventive examples herein below.

DISCLOSURE OF THE INVENTION

Cobalt-Containing Catalyst Composition

According to a first aspect of the invention, there is provided a cobalt-containing catalyst composition comprising cobalt and/or a cobalt compound supported on and/or in a silica ($SiO_2$) catalyst support wherein the average pore diameter of the catalyst support is more than 20 nm but less than 50 nm; the catalyst composition also including a titanium compound on and/or in the catalyst support, and a manganese compound on and/or in the catalyst support.

The catalyst composition may be a hydrocarbon synthesis catalyst composition for synthesising hydrocarbons and/or oxygenates of hydrocarbons from at least hydrogen and carbon monoxide. Preferably, the catalyst composition is a Fischer-Tropsch (FT) synthesis catalyst composition for performing Fischer-Tropsch synthesis. The FT synthesis may be performed in a fixed bed reactor, a slurry bed reactor or a fixed fluidized bed reactor. Preferably, the FT synthesis is a three-phase slurry bed FT synthesis process.

In one embodiment of the invention, the catalyst composition may include a cobalt compound in which case the catalyst composition may be a catalyst precursor. The cobalt compound may be a cobalt salt, alternatively it is a cobalt oxide. The cobalt salt may comprise any suitable cobalt salt such as cobalt hydroxide and/or cobalt nitrate. The cobalt oxide may be selected from the group consisting of CoO, CoO(OH), $Co_3O_4$, $Co_2O_3$ and a mixture of two or more thereof. Preferably, the cobalt oxide is $Co_3O_4$.

In another embodiment of the invention, the catalyst composition may include cobalt with a zero valency in which case the catalyst composition may be an active catalyst. The cobalt may be in the form of particles or preferably crystallites distributed over a support surface.

The catalyst precursor or the catalyst may contain cobalt (Co) at a loading of from 5 to 70 g Co/100 g catalyst support, preferably from 20 to 40 g Co/100 g catalyst support, and more preferably from 25 to 35 g Co/100 g catalyst support.

The catalyst composition may also include a dopant, preferably a dopant capable of enhancing the reducibility of a cobalt compound. The dopant may be in the form of a dopant compound which is a compound of a metal selected from the group including palladium (Pd), platinum (Pt), ruthenium (Ru), rhenium (Re) and a mixture of two or more thereof. The mass proportion of the metal of the dopant (especially palladium metal or platinum metal) to the cobalt metal may be from 1:300 to 1:3000.

The silica ($SiO_2$) catalyst support may be a precipitated silica support. Preferably it is a fumed (it may also be referred to as a pyrogenic) silica support or a silica gel support. Preferably it is an amorphous silica support especially an amorphous fumed silica support or an amorphous silica gel support.

The silica catalyst support is a porous support and preferably it is also pre-shaped.

Preferably the silica support has an average pore diameter of more than 22 nm, preferably at least 25 nm, preferably less than 40 nm, preferably from 25 to 35 nm, preferably 30 nm. The average pore diameter was determined by means of Barrett-Joyner-Halenda (BJH) nitrogen physisorption analysis. It will be appreciated that the average pore diameter is the average pore diameter of the support prior to the addition of any one or more of the titanium compound, the manganese compound and the cobalt compound.

The support pore volume may be between 0.1 and 1 ml/g catalyst support, preferably between 0.3 and 0.9 ml/g catalyst support.

The pre-shaped support may be a particulate support, preferably with an average particle size of between 1 and 500 micrometers, preferably between 10 and 250 micrometers, still more particularly from 45 to 200 micrometers.

Preferably, the catalyst composition includes more than 1 wt % and not more than 10 wt % Ti, based on the weight of the silica ($SiO_2$) catalyst support (excluding the weight of the Ti and Mn), the Ti being present in the form of one or more titanium compounds.

Preferably, the catalyst composition does not include more than 5 wt % Ti, preferably not more than 3.5 wt % Ti. Preferably, titanium, in the form of the one or more titanium compounds, may be present in and/or on the catalyst support in an amount of more than 1.5 wt %, preferably at least 2.0 wt %, more preferably at least 2.4 wt % Ti.

Preferably, titanium, in the form of the one or more titanium compounds, may be present in and/or on the catalyst support in an amount of less than 3.5 wt %, preferably not more than 3.0 wt %, but preferably more than 2.0 wt % Ti.

The preferred amount of titanium, in the form of the one or more titanium compounds, present in and/or on the catalyst support is 2.6 wt % Ti. The Ti is preferably present as titanium oxide.

Preferably, the Ti is included as a support modifier, that is as Ti which has been introduced onto and/or into the catalyst support (and preferably also calcined) prior to a cobalt compound having been introduced onto and/or into the catalyst support.

Alternatively, the Ti may be included as a promoter, that is, as Ti which has been introduced onto and/or into the catalyst support during and/or subsequent to a cobalt compound having been introduced onto and/or into the catalyst support.

Preferably, the catalyst composition includes more than 0.5 wt % and less than 10 wt % Mn, based on the weight of the silica ($SiO_2$) catalyst support (excluding the weight of the Ti and Mn), the Mn being present in the form of one or more manganese compounds.

Preferably, the catalyst composition does not include more than 7.5 wt % Mn, preferably not more than 5 wt % Mn. Preferably, manganese, in the form of the one or more manganese compounds, may be present in and/or on the catalyst support in an amount of more than 1 wt %, preferably at least 1.5 wt %, more preferably at least 1.8 wt % Mn.

Preferably, manganese, in the form of the one or more manganese compounds, may be present in and/or on the catalyst support in an amount of less than 5 wt %, preferably not more than 3.5 wt %, but preferably more than 1.8 wt % Mn.

The preferred amount of manganese, in the form of the one or more manganese compounds, present in and/or on the catalyst support is 3.1 wt % Mn. The manganese is preferably present as manganese oxide.

The Mn may be included as a promoter, that is, as Mn which has been introduced onto and/or into the catalyst support during and/or subsequent to a cobalt compound having been introduced onto and/or into the catalyst support.

Alternatively, the Mn may be included as a support modifier, that is, as Mn which has been introduced onto and/or into the catalyst support (and preferably also calcined) prior to a cobalt compound having been introduced onto and/or into the catalyst support.

In one embodiment of the invention, the catalyst composition includes no or substantially no Re. Preferably, if any Re is present in the catalyst composition, the Re to Co weight ratio is below 0.001:1.

Process for Preparing a Cobalt-Containing Catalyst Precursor

According to a second aspect of the present invention, there is provided a process for preparing a cobalt-containing catalyst precursor, the process comprising introducing a cobalt compound onto and/or into a silica ($SiO_2$) catalyst support wherein the average pore diameter of the catalyst support is more than 20 nm but less than 50 nm; prior to and/or during and/or subsequent to introducing the cobalt compound onto and/or into the catalyst support, introducing a titanium compound onto and/or into the catalyst support; and prior to, and/or during, and/or subsequent to introducing the cobalt compound onto and/or into the catalyst support, introducing a manganese compound onto and/or into the catalyst support, thereby providing a cobalt-containing catalyst precursor.

It will be appreciated that by introducing a compound onto and/or into a catalyst support the compound may be contacted with a precursor compound of the support or it may be contacted with the support itself.

The catalyst precursor is preferably a catalyst precursor as described above. The process preferably includes one or more calcination steps wherein at least the titanium and manganese compounds introduced into and/or onto the catalyst support are converted to titanium oxide and manganese oxide respectively.

The silica ($SiO_2$) catalyst support is preferably a catalyst support as described above.

Preparing a Titanium-Containing Catalyst Support

The titanium compound may be introduced onto and/or into the catalyst support by preparing a titanium-containing catalyst support material by contacting a silicon-based catalyst support material (preferably silica ($SiO_2$)) with a titanium compound; and calcining the titanium-containing catalyst support material at a temperature above 200° C. to obtain a silica ($SiO_2$) catalyst support which includes Ti in the form of one or more titanium compounds.

Contacting the Catalyst Support Material with the Titanium Compound

The silicon-based catalyst support material may be selected from the group consisting of a silicon-based catalyst support precursor which is convertible to a silica ($SiO_2$) catalyst support upon calcination thereof; and a silica ($SiO_2$) catalyst support.

When the silicon-based catalyst support material is a silicon-based catalyst support precursor, the titanium compound is preferably introduced onto and/or into the catalyst support (and preferably also calcined) prior to introducing the cobalt compound onto and/or into the catalyst support. In this embodiment, the titanium may serve as a support modifier.

The catalyst support precursor may be shaped into particulate form after the introduction of the titanium compound onto and/or into the catalyst support precursor and preferably before calcination thereof. The shaping may, for example, be carried out by means of spray drying. Prior to shaping the catalyst support precursor, it may be partially dried. The resulting shaped product may then be subjected to the calcination above 200° C. in order to convert the catalyst support precursor to a catalyst support. The calcination may take place prior to introducing the cobalt compound onto and/or into the shaped product. In order to achieve a desired particle size distribution, classification may be performed on the shaped particulate product, using, for example, cyclones or sieves.

However, the silicon-based catalyst support material is preferably a silica ($SiO_2$) catalyst support. The catalyst support is preferably suitable for use as a support in a catalyst for synthesising hydrocarbons and/or oxygenates of hydrocarbons from at least hydrogen and carbon monoxide, particularly a Fischer-Tropsch (FT) synthesis catalyst.

The FT synthesis catalyst may be for use in a process to be performed in a fixed bed reactor, slurry bed reactor or even a fixed fluidized bed reactor. Preferably, the process is to be performed in a three-phase slurry bed FT synthesis reactor.

In a preferred embodiment of the invention, the catalyst support or catalyst support precursor may be contacted with the titanium compound (and preferably also calcined) prior to introducing the cobalt compound onto and/or into the catalyst support. In this embodiment, the titanium may serve as support modifier. Preferably, the calcination of the titanium containing catalyst support material also takes place prior to introducing the cobalt compound onto and/or into the catalyst support.

In an alternative embodiment of the invention, the catalyst support or catalyst support precursor may be contacted with the titanium compound during and/or subsequent to introducing the cobalt compound onto and/or into the catalyst support. In this embodiment, the titanium may serve as a promoter. The calcination of the titanium containing catalyst support material then takes place subsequent to introducing the cobalt compound onto and/or into the catalyst support.

The catalyst support may be as described herein above.

As set out above, the catalyst support material is contacted with a titanium compound. The titanium compound may be an inorganic titanium compound, but preferably it is an organic titanium compound.

When referred to in this specification, an organic titanium compound should be understood to be a titanium compound wherein titanium is associated with at least one organic group by means of a bond, for instance by means of a covalent bond, a metal-to-ligand coordination or an ionic interaction.

Preferably, in the organic titanium compound, titanium is associated with at least one non-carbon atom of the at least one organic group, in particular with an oxygen atom of the organic group.

In one embodiment of the invention, at least one organic group of the organic titanium compound may be a chelating compound, preferably a chelating compound which binds to titanium by means of at least one non-carbon atom, preferably an oxygen atom (preferably by means of two oxygen atoms). Preferably, all the groups associated with the titanium are organic groups, and preferably all the said organic groups are associated with the titanium via an oxygen atom.

In one embodiment of the invention some, but preferably all, of the organic groups are of the formula —(O)—R where R is an organic group. R in different —(O)—R groups may be the same or different. R of an —(O)—R group may be bound, or may not be bound, to R of another —(O)—R group.

R may be an acyl or hydrocarbyl group or it may be a heterohydrocarbyl group (that is, an organic group consisting of carbon, hydrogen and at least one atom which is not carbon or hydrogen), preferably a hydrocarbyl group, preferably an alkyl group, and preferably an alkyl group with not more than eight carbon atoms.

Alternatively, R may be of the formula —$OR^1$ where $R^1$ may be a hydrocarbyl group or it may be a heterohydrocarbyl group (that is, an organic group consisting of carbon, hydrogen and at least one atom which is not carbon or hydrogen), preferably an alkyl group, preferably an alkyl group and preferably an alkyl group with not more than eight carbon atoms.

In one embodiment of the invention, the organic titanium compound may be selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato) dihydroxide.

The contacting of the catalyst support material with the titanium compound may be by any suitable method including, for example, impregnation, precipitation, adsorption or chemical vapour phase deposition.

Preferably, the contacting of the titanium compound with the catalyst support material is by means of impregnation. A suitable impregnating liquid medium may be used to effect the contact between the titanium compound and the catalyst support material. The impregnation may be incipient wetness impregnation, but preferably it is slurry phase impregnation. Preferably, the liquid medium is a non-aqueous medium, such as an organic liquid medium, and preferably it is an alcohol such as ethanol. Alternatively, the liquid medium is an inorganic liquid medium, such as water. Preferably, the liquid medium is a solvent for the titanium compound.

The impregnation is preferably carried out at a temperature above 25° C. The temperature may be 50-60° C. The impregnation may be carried out for a period of from 1 minute to 20 hours, preferably from 1 minute to 5 hours. The impregnation may be effected at atmospheric pressure.

After impregnation, the excess impregnating liquid medium may be removed, preferably by means of drying. The drying is preferably carried out at sub-atmospheric conditions, preferably from 0.01 to 0.9 bar(a). The drying is preferably carried out at temperature above 25° C., more preferably at a temperature of not more than 125° C.

Calcination of the Titanium-Containing Support Material

The calcination of the titanium-containing catalyst support material may take place in a non-reducing environment, preferably in an oxidizing environment, such as in air. The calcination may be carried out either in a stationary or in a fluidized bed calciner. The calcination may instead take place in a rotary kiln. Most preferred, however, is a rotary kiln. The calcination may typically take place for a period of 10 minutes to 10 hours.

During the calcination of the titanium-containing catalyst support material prepared by contacting the catalyst support material with the titanium compound, the titanium compound in and/or on the catalyst support material may react and/or it may decompose and/or it may bond chemically to the catalyst support material; however, preferably, the calcination transforms the titanium compound to a titanium oxide, preferably by decomposition and/or reaction.

When the titanium compound is introduced onto and/or into the catalyst support prior to introducing the cobalt compound onto and/or into the catalyst support, the calcination of the titanium-containing support material is preferably carried out at or above 350° C., preferably at at least 400° C., more preferably at above 500° C., still more preferably at least 525° C. Preferably, the calcination is carried out below 1200° C., preferably below 950° C. When the titanium compound is introduced onto and/or into the catalyst support during and/or subsequent to introducing the cobalt compound onto and/or into the catalyst support the calcination of the titanium-containing support material is preferably carried out in the manner described below for calcination subsequent to introducing the cobalt compound onto and/or into the catalyst support.

Ti level after calcination may be as described herein above.

In one preferred embodiment of the invention, the titanium compound may be introduced onto and/or into the catalyst support (and preferably also calcined) prior to introducing the cobalt compound onto and/or into the catalyst support. In this embodiment, the titanium may serve as support modifier. Alternatively the titanium compound may be introduced onto and/or into the catalyst support during and/or subsequent to introducing the cobalt compound onto and/or into the catalyst support. In this embodiment, the titanium may serve as a promoter.

Preparing the Manganese-Containing Catalyst Support

The manganese compound may be introduced onto and/or into the catalyst support by preparing a manganese-containing catalyst support material by contacting a silicon-based catalyst support material (preferably silica ($SiO_2$)) with a manganese compound; and calcining the manganese-containing catalyst support material at a temperature above 180° C. to obtain a silica ($SiO_2$) catalyst support which includes Mn in the form of one or more manganese compounds.

Contacting the Catalyst Support Material with the Manganese Compound

The silicon-based catalyst support material may be selected from the group consisting of a silicon-based catalyst support precursor which is convertible to a silica ($SiO_2$) catalyst support upon calcination thereof; and a silica ($SiO_2$) catalyst support.

When the silicon-based catalyst support material is a silicon-based catalyst support precursor, the manganese compound is preferably introduced onto and/or into the catalyst support (and preferably also calcined) prior to introducing the cobalt compound onto and/or into the catalyst support. In this embodiment, the manganese may serve as a support modifier.

The silicon-based catalyst support precursor may be shaped into particulate form after the introduction of the manganese compound onto and/or into the catalyst support precursor and preferably before calcination thereof. The shaping may, for example, be carried out by means of spray drying. Prior to shaping the catalyst support precursor, it may be partially dried. The resulting shaped product may then be subjected to the calcination in order to convert the catalyst support precursor to a catalyst support. The calcination may take place prior to introducing the cobalt compound onto and/or into the shaped product. In order to achieve a desired particle size distribution, classification may be performed on the shaped particulate product, using, for example, cyclones or sieves.

However, the silicon-based catalyst support material is preferably a silica ($SiO_2$) catalyst support. The catalyst support is preferably as described herein above.

In one embodiment of the invention, the catalyst support or catalyst support precursor may be contacted with the manganese compound prior to introducing the cobalt compound onto and/or into the catalyst support. In this embodiment, the manganese may serve as a support modifier. Preferably, the calcination of the manganese containing catalyst support material also takes place prior to introducing the cobalt compound onto and/or into the catalyst support.

In an alternative embodiment of the invention, the catalyst support or catalyst support precursor may be contacted with the manganese compound during and/or subsequent to introducing the cobalt compound onto and/or into the catalyst support. In this embodiment of the invention, the manganese may serve as a promoter. The calcination of the manganese containing catalyst support material then takes place subsequent to introducing the cobalt compound onto and/or into the catalyst support.

Preferably, the catalyst support or catalyst support precursor is contacted with the manganese compound after the titanium compound has been introduced onto and/or into the catalyst support.

The catalyst support may be as described herein above.

As set out above, the catalyst support material is contacted with a manganese compound. The manganese compound may be an inorganic manganese compound, such as manganese nitrate. Alternatively, it may be an organic manganese compound.

In this specification, an organic manganese compound is a manganese compound wherein manganese is associated with at least one organic group by means of a bond, for instance by means of a covalent bond, a metal-to-ligand coordination or an ionic interaction.

Preferably, in the organic manganese compound, manganese is associated with at least one non-carbon atom of the at least one organic group, in particular with an oxygen atom of the organic group. Preferably, all the groups associated with the manganese are organic groups, and preferably all the said organic groups are associated with the manganese via an oxygen atom. The manganese compound may be selected from the group consisting of manganese(II)acetate tetrahydrate, manganese(II)ethoxide and manganese(II) methoxide.

The contacting of the catalyst support material with the manganese compound may be by any suitable method including, for example, impregnation, precipitation, adsorption or chemical vapour phase deposition.

Preferably, the contacting of the manganese compound with the catalyst support material is by means of impregnation. A suitable impregnating liquid medium may be used to effect the contact between the manganese compound and the catalyst support material. The impregnation may be incipient wetness impregnation. In a preferred alternative embodiment the impregnation may be slurry phase impregnation. Preferably, the liquid medium is an inorganic liquid medium, such as water. Preferably, the liquid medium is a solvent for the manganese compound.

After impregnation, the excess impregnation liquid medium may be removed, preferably by means of drying. The drying is preferably carried out at sub-atmospheric conditions, preferably from 0.01 to 0.9 bar(a). The drying is preferably carried out at a temperature above 25° C., more preferably at a temperature of not more than 125° C.

Calcination of the Manganese-Containing Support Material

The calcination of the manganese-containing catalyst support material may take place in a non-reducing environment, preferably in an oxidizing environment, such as in air. The calcination may be carried out either in a stationary or in a fluidized bed calciner. The calcination may instead take place in a rotary kiln. In a preferred embodiment, the calcination is carried out in a fluidized bed calciner. The calcination may typically take place for a period of 10 minutes to 10 hours.

During the calcination of the manganese-containing catalyst support material prepared by contacting the catalyst support material with the manganese compound, the manganese compound in and/or on the catalyst support material may react and/or it may decompose and/or it may bond chemically to the catalyst support material; however, preferably, the calcination transforms the manganese compound to a manganese oxide, preferably by decomposition and/or reaction.

When the manganese compound is introduced onto and/or into the catalyst support prior to introducing the cobalt compound onto and/or into the catalyst support, the calcination of the manganese-containing support material is preferably carried out at or above 350° C., preferably at at least 400° C., more preferably at above 500° C., still more preferably the calcination is carried out at at least 525° C. Preferably the calcination is carried out below 1200° C., preferably below 950° C. When the manganese compound is introduced onto and/or into the catalyst support during and/or subsequent to introducing the cobalt compound onto and/or into the catalyst support, the calcination of the manganese-containing support material is preferably carried out in the manner described below for calcination subsequent to introducing the cobalt compound onto and/or into the catalyst support.

The Mn level after calcination may be as described herein above.

In one embodiment of the invention, the manganese compound may be introduced onto and/or into the catalyst support (and preferably also calcined) prior to introducing the cobalt compound onto and/or into the catalyst support. In this embodiment, the manganese may serve as support modifier. Alternatively the manganese compound may be introduced onto and/or into the catalyst support during and/or subsequent to introducing the cobalt compound onto and/or into the catalyst support. In this embodiment, the manganese may serve as a promoter.

In a preferred embodiment of the invention, the titanium compound is introduced onto and/or into the catalyst support (and preferably also calcined) prior to introducing the cobalt compound onto and/or into the catalyst support. In this embodiment, the titanium may serve as a support modifier.

The titanium compound and manganese compound may be introduced separately or simultaneously onto and/or into the catalyst support. In one embodiment the manganese compound is introduced onto and/or into the catalyst support before or with introducing the titanium compound onto and/or into the catalyst support. In another embodiment the manganese compound is introduced onto and/or into the catalyst support after the titanium compound has been introduced onto and/or into the catalyst support.

In one embodiment the manganese compound may be introduced onto and/or into the catalyst support which contains the titanium compound, the manganese compound being introduced during and/or subsequent to introducing the cobalt compound onto and/or into the catalyst support which contains the titanium compound. In last-mentioned embodiment, the manganese may serve as a promoter.

Introducing the Cobalt Compound onto and/or into the Catalyst Support

The cobalt compound may be introduced onto and/or into the catalyst support by contacting the cobalt compound with the catalyst support in any suitable manner, but preferably it is by means of impregnation. Preferably, the impregnation is carried out by forming a mixture of the cobalt compound, a liquid carrier for the cobalt compound and the catalyst support.

The liquid carrier may comprise a solvent for the cobalt compound and preferably the said cobalt compound is dissolved in the liquid carrier. The liquid carrier may be water.

The impregnation may be effected by any suitable impregnation method, including incipient wetness impregnation or slurry phase impregnation. Slurry phase impregnation is preferred.

Preferably, the cobalt compound is dissolved in the liquid carrier in order that the volume of the solution is greater than xy litre, which solution is then mixed with the catalyst support, and wherein x is the BET pore volume of the catalyst support in l/kg support, and y is the mass of the catalyst support to be impregnated in kg. Preferably, the volume of the solution is greater than 1.5xy litre ("l"), and preferably it is about 2xy litre.

The impregnation may be carried out at sub-atmospheric pressure, preferably below 85 kPa(a), preferably at 20 kPa(a) and lower. Preferably, the impregnation is also carried out at a temperature above 25° C. The impregnation temperature may be above 40° C., preferably above 60° C., but preferably not above 95° C.

The impregnation may be followed by at least partial drying of the impregnated support, preferably at a temperature above 25° C. The drying temperature may be above 40° C., preferably above 60° C., but preferably not above 95° C. Preferably, the drying may be effected at sub-atmospheric conditions, preferably below 85 kPa(a), preferably at 20 kPa(a) or lower.

In one embodiment of the invention, the impregnation and at least partial drying of the catalyst support may be carried out using a procedure which includes a first step wherein the catalyst support is impregnated (preferably slurry impregnated) with the cobalt compound at a temperature above 25° C., and at sub-atmospheric pressure, and the resultant product is dried; and at least one subsequent step wherein the resulting, at least partially dried impregnated catalyst support of the first step, is subjected to treatment at a temperature above 25° C., and sub-atmospheric pressure such that the temperature of the subsequent step exceeds that in the first step and/or the sub-atmospheric pressure in the subsequent step is lower than that in the first step. This two step impregnation procedure may be as described in WO 00/20116, which is incorporated herein by reference.

A dopant capable of enhancing the reducibility of the cobalt of the cobalt compound may also be introduced onto and/or into the catalyst support. The dopant may be introduced during or after the introduction of the cobalt compound onto and/or into the catalyst support. The dopant may be introduced as a dopant compound which is a compound of a metal selected from the group consisting of palladium (Pd), platinum (Pt), ruthenium (Ru), rhenium (Re) and a mixture of two or more thereof. Preferably, the dopant compound is an inorganic salt. Preferably, the dopant is soluble in water. The mass proportion of the metal of the dopant to the cobalt metal may be as set out above.

The cobalt compound introduced onto and/or into the catalyst support may be any suitable cobalt compound. Preferably, it is an inorganic compound, more preferably an inorganic salt of cobalt. The cobalt compound may be cobalt nitrate, and particularly it may be $Co(NO_3)_2 \cdot 6H_2O$.

In an alternative embodiment of the invention, the cobalt compound may be introduced onto and/or into the catalyst support by contacting an insoluble cobalt compound (such as cobalt hydroxide) with the catalyst support, preferably by forming a slurry of particles of the insoluble cobalt compound, with particles of the catalyst support in a carrier liquid; and removing carrier liquid from the slurry to obtain a dried product which is then calcined. The process may also include the step of adding a cobalt compound in the form of a soluble cobalt compound (such as cobalt nitrate). Preferably the soluble cobalt compound is included in the slurry of particles of the insoluble cobalt compound, with particles of the catalyst support in the carrier liquid.

The process may also include the step of introducing an acid, preferably a carboxylic acid, preferably a multi-functional carboxylic acid having the general formula (1)

$$HOOC—C^*R_1C^*R_2—COOH \qquad (1)$$

or a precursor thereof, where
C* in each of $C^*R_1$ and $C^*R_2$ is a $sp^2$ carbon, and $R_1$ and $R_2$ are the same or different, and each are selected from the group consisting of hydrogen and an organic group, into and/or onto the catalyst support prior to or simultaneously with the cobalt compound.

Preferably, the ratio of the quantity of carboxylic acid used relative to the support surface area of the catalyst support is at least 0.3 µmol carboxylic acid/m² of support surface area.

In principle, any multi-functional carboxylic acid complying with formula (1) can be used, or a precursor thereof such as an anhydride. Non-limiting examples of suitable carboxylic acids are maleic acid, mesaconic acid, citraconic acid and fumaric acid. Preferably, maleic acid may be used. An example of a suitable acid precursor is maleic anhydride. Mixtures of acids of formula (1) or precursors thereof may also be used, as may mixtures of acids of formula (1) or precursors thereof with acids, or precursors thereof, which do not comply with formula (1).

The catalyst support with the cobalt compound thereon and/or therein may be calcined. Preferably the calcination is performed after a drying step. The calcination may be effected in order to decompose the cobalt compound and/or to cause it to react with oxygen. During calcination an oxide or oxides of the cobalt may be formed. For example, a cobalt compound (for example, cobalt nitrate or cobalt hydroxide) may be converted into a compound selected from CoO, CoO(OH), $CoO_4$, $Co_2O_3$ or a mixture of two or more thereof.

The calcination may be carried out in any suitable manner such as in a rotary kiln, but preferably it is carried out in a fluidised bed reactor or calciner.

The calcination may be carried out in an inert atmosphere, but preferably it is carried out in an oxidizing atmosphere, preferably in the presence of oxygen, more preferably in air.

Preferably the calcination is carried out at a temperature above 95° C., more preferably above 120° C., still more preferably above 200° C., but preferably not above 400° C., more preferably not above 300° C.

The calcination may be carried out by using a heating rate and an air space velocity that comply with the following criteria:
(i) when the heating rate is ≤1° C./min, the air space velocity is at least 0.76 $Nm^3$/(kg $Co(NO_3)_2 \cdot 6H_2O$)/h; and
(ii) when the heating rate is higher than 1° C./min, the air space velocity satisfies the relation:

$$\log(\text{space velocity}) \geq \log 0.76 + \log 20 - \log 0.76/2 \log(\text{heating rate})$$

The impregnation, the at least partial drying and calcination may be repeated to achieve higher loadings of the cobalt compound onto and/or into the catalyst support. In one embodiment of the invention, a first impregnation, drying and calcination procedure may be followed by a partial reduction procedure of the calcined material; and the partially reduced material may then be subjected to a further impregnation, drying and calcination procedure. The partial reduction procedure may be executed with a final temperature of between 100° C. and 300° C.

In one embodiment of the invention, the cobalt compound may be introduced onto and/or into the catalyst support by a method which includes in a first preparation step, impregnating the catalyst support with an organic cobalt compound in a carrier liquid, at least partially drying the impregnated support, and calcining the at least partially dried impregnated support, to obtain a calcined intermediate; and in a second preparation step, impregnating the calcined intermediate from the first preparation step, with an inorganic cobalt compound in a carrier liquid, at least partially drying the impregnated support, and calcining the at least partially dried impregnated support, to obtain the catalyst precursor.

Activation

According to a third aspect of the present invention, there is provided a process for preparing a cobalt-containing catalyst, the process comprising preparing a cobalt-containing catalyst precursor as set out above; and reducing the catalyst precursor, thereby activating the catalyst precursor.

The reduction of the catalyst precursor preferably includes treating it with a reducing gas to activate it. Preferably, the reducing gas is hydrogen or a hydrogen containing gas. The hydrogen containing gas may consist of hydrogen and one or more inert gases which are inert in respect to the active catalyst. The hydrogen containing gas preferably contains at least 90 volume % hydrogen.

The reducing gas may be contacted with the catalyst precursor in any suitable manner. Preferably the catalyst precursor is provided in the form of a bed of particles with the reducing gas being caused to flow through the bed of particles. The bed of particles may be a fixed bed, but preferably it is a fluidised bed and preferably the reducing gas acts as the fluidising medium for the bed of catalyst precursor particles.

The reduction may be carried out at a pressure from 0.6 to 1.5 bar(a), preferably from 0.8 to 1.3 bar(a). Alternatively, the pressure may be from 1.5 bar(a) to 20 bar(a). Preferably, however, the pressure is at about atmospheric pressure.

The reduction is preferably carried out at a temperature above 25° C. at which the catalyst precursor will be reduced to an active form. Preferably, the reduction is carried out at a temperature above 150° C., and preferably below 600° C. Preferably the reduction is carried out at a temperature below 500° C., more preferably below 450° C.

During reduction the temperature may be varied, and preferably it is increased to a maximum temperature as set out above.

The flow of the reducing gas through the catalyst bed is preferably controlled to ensure that contaminants produced during reduction are maintained at a sufficiently low level. The reducing gas may be recycled, and preferably the recycled reducing gas is treated to remove one or more contaminants produced during reduction. The contaminants may comprise one or more of water and ammonia.

The reduction may be carried out in two or more steps during which one or both of the heating rate and the space velocity of the reducing gas is varied.

In one embodiment of the invention, the active catalyst may be coated preferably by introducing a mixture of active catalyst particles and a coating medium in the form of a molten organic substance, which is at a temperature $T_1$, and which sets or congeals at a lower temperature $T_2$ so that $T_2 < T_1$, into at least one mould; and at least partly submerging the mould in a cooling liquid, so as to cool the organic substance down to a temperature $T_3$, where $T_3 \leq T_2$.

During the reduction, the water partial pressure is preferably kept as low as possible, more preferably below 0.1 atmosphere. The hydrogen space velocity may be from 2 to 4 liters per hour per gram of catalyst.

In one embodiment of the present invention, the process for preparing the cobalt-containing catalyst may include
  in a carbide formation step, treating the activated catalyst, comprising the catalyst support supporting cobalt with a zero valency, with a CO containing gas (preferably at a temperature $T_1$, where $T_1$ is from 200° C. to 280° C.) to convert the cobalt to cobalt carbide thereby obtaining a cobalt carbide containing catalyst precursor; and
  in a subsequent activation step, subjecting the cobalt carbide containing catalyst precursor to treatment with a hydrogen containing gas (preferably at a temperature $T_2$, where $T_2$ is at least 300° C.) to convert the cobalt carbide to cobalt metal thereby activating the cobalt carbide containing catalyst precursor and obtaining a cobalt-containing hydrocarbon synthesis catalyst.

The catalyst is preferably a catalyst as described above.

Hydrocarbon Synthesis

According to a fourth aspect of the present invention, there is provided a hydrocarbon synthesis process which comprises contacting a cobalt-containing catalyst as set out above with hydrogen and carbon monoxide at a temperature above 100° C. and at a pressure of at least 10 bar with the catalyst, to produce hydrocarbons and optionally, oxygenates of hydrocarbons.

According to a fifth aspect of the present invention, there is provided a hydrocarbon synthesis process for producing hydrocarbons and, optionally, oxygenates of hydrocarbons, which process includes contacting a synthesis gas comprising hydrogen, carbon monoxide and N-containing contaminants selected from the group consisting of HCN, $NH_3$, NO, $R_xNH_{3-x}$ where R is an organic group and x is 1, 2 or 3, with R being the same or different when x is 2 or 3, $R^1$—CN where $R^1$ is an organic group, and heterocyclic compounds containing at least one nitrogen atom as a ring member of a heterocyclic ring of the heterocyclic compound, with the N-containing contaminants constituting, in total, at least 100 vppb but less than 1 000 000 vppb of the synthesis gas, at a temperature of at least 180° C. and a pressure of at least 10 bar(a) (1000 kPa(a)), with a catalyst as set out above to obtain hydrocarbons and, optionally, oxygenates of hydrocarbons, by means of Fischer-Tropsch synthesis reaction of the hydrogen with the carbon monoxide.

The synthesis gas (syngas) may contain, in total, at least 200 vppb N-containing contaminants. Preferably, the syngas contains at least 250 vppb N-containing contaminants. More preferably, the syngas contains at least 500 vppb N-containing contaminants. Typically, the syngas contains at least 1000 vppb N-containing contaminants. Preferably, the syngas contains not more than 100 000 vppb N-containing contaminants. More preferably, the syngas contains not more than 20 000 vppb N-containing contaminants. Typically, the syngas may contain not more than 10 000 vppb N-containing contaminants. For example, in one embodiment of the invention, the syngas may contain about 2000 vppb N-containing contaminants. However, in another embodiment, the syngas may contain about 5000 vppb N-containing contaminants. Typically, when the syngas is that of a gas-to-liquid process, it contains HCN and $NH_3$ as N-containing contaminants; when it is that of a coal-to-liquid process, it contains $NH_3$ and NO as N-containing contaminants.

Preferably, R in $R_xNH_{3-x}$ is a hydrocarbyl group and/or an oxygenated hydrocarbyl group. More preferably, R in $R_xNH_{3-x}$ is an alkyl group and/or an alcohol. Preferably, x is 1 or 2. In a preferred embodiment of the invention $R_xNH_{3-x}$ is dipropylamine $(CH_3CH_2CH_2)_2NH$. Alternatively, $R_xNH_{3-x}$ can be diethanolamine or methyl-diethanolamine.

Preferably, $R^1$ in $R^1$—CN is a hydrocarbyl group. More preferably, $R^1$ in $R^1$—CN is an alkyl group. In one preferred embodiment of the invention, $R^1$ is methyl.

The heterocyclic compounds may include oxygen containing groups. Examples of such oxygen containing compounds and non-oxygen containing compounds are 4-piperidineoacetophenone (heterocyclic with oxygen), 1,4-bipiperidine (heterocyclic, no oxygen), 1-piperidinepropionitrile (monocyclic), and 3-piperidino-1, 2-propanediol (monocyclic with oxygen).

Alternatively the hydrocarbon synthesis process may be as set out above except that the synthesis gas contains no or less than 100 vppb of the N-containing contaminants as set out above.

In one preferred embodiment of the invention the catalyst may have been prepared by including
  in a carbide formation step, treating the activated catalyst, comprising the catalyst support supporting cobalt with a zero valency, with a CO containing gas (preferably at a temperature $T_1$, where $T_1$ is from 200° C. to 280° C.) to convert the cobalt to cobalt carbide thereby obtaining a cobalt carbide containing catalyst precursor; and
  in a subsequent activation step, subjecting the cobalt carbide containing catalyst precursor to treatment with a hydrogen containing gas (preferably at a temperature $T_2$, where $T_2$ is at least 300° C.) to convert the cobalt carbide to cobalt metal thereby activating the cobalt carbide containing catalyst precursor and obtaining a cobalt-containing hydrocarbon synthesis catalyst.

Preferably the hydrocarbon synthesis process is a Fischer-Tropsch process, preferably a three phase Fischer-Tropsch process, more preferably a slurry bed Fischer-Tropsch process for producing a wax product.

The water partial pressure in the slurry bed may reach at least 5 bar(a), preferably at least 8 bar(a). The total feed $H_2/CO$ molar ratio may be from 1.4 to 2, preferably about 1.5, alternatively about 1.8. In an alternative embodiment, the water partial pressure in the slurry bed may be below 5 bar(a). The total feed $H_2/CO$ molar ratio may be from 1.4 to 2, preferably about 1.6.

The hydrocarbon synthesis process may also include a hydroprocessing step for converting the hydrocarbons and optionally oxygenates thereof to liquid fuels and/or other chemicals.

According to yet another aspect of the present invention, there is provided products produced by the hydrocarbon synthesis process as described above.

The catalyst as described above may be used to improve the activity stability or activity or productivity of a hydrocarbon synthesis process. The improvement may be over a catalyst which does not include titanium and manganese. The titanium and manganese present in the catalyst may reduce the deactivation of the catalyst during hydrocarbon synthesis. The improved activity stability, activity, C5+ productivity and reduced deactivation may be measured after three and/or more days of hydrocarbon synthesis. The titanium and manganese present in the catalyst may serve to reduce methane selectivity and/or may reduce support dissolution of the support during hydrocarbon synthesis.

The C5+ productivity is the unit mass of C5+ hydrocarbons per unit catalyst per unit time and is a function of the rate of CO converted and the C5+ hydrocarbon selectivity of the catalyst.

BRIEF DESCRIPTION OF THE FIGURES

The invention will now be described in more detail, by way of example only, with reference to the accompanying figures in which.

Figure 1:
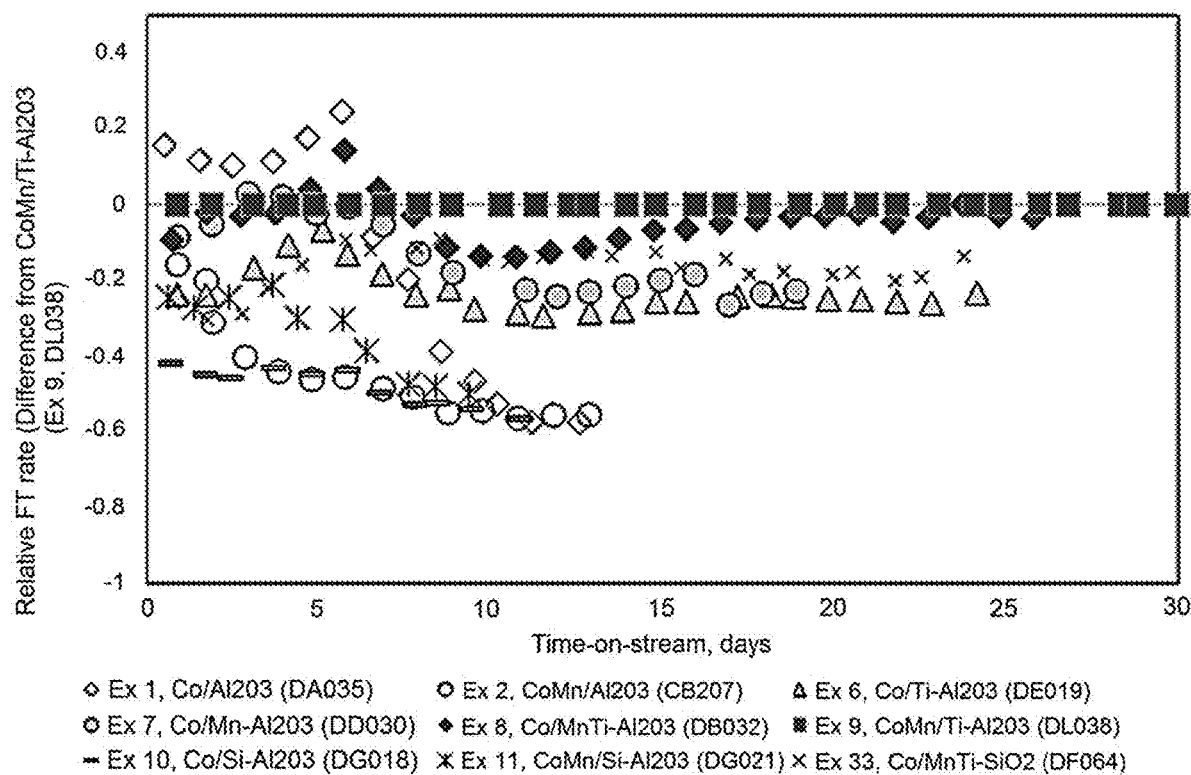
FIG. 1: is a graph showing the FT rate over Examples 1, 2, 6-8, 10, 11 and 33 relative to Example 9.

The foregoing and other objects, features and advantages of the present invention will become more apparent from the following description of certain embodiments of the present invention by way of the following non-limiting examples.

EXAMPLES

The invention will now be described with reference to the following non-limiting experimental examples.

Example 1 (Comparative)—30 g Co/0.04 g Pt/100 g un-modified $Al_2O_3$

A cobalt based Fischer-Tropsch synthesis catalyst precursor with the composition 30 g Co/0.04 g Pt/100 g support was prepared using an un-modified $Al_2O_3$ (Puralox with a surface area of 150 $m^2/g$—hereinafter referred to as Puralox) support.

In a first impregnation step $Co(NO_3)_2.6H_2O$ (79.0 g) and $(NH_4)_3Pt(NO_3)_2$ (0.026 g) were dissolved in distilled water (100 g). Maleic acid in the amount of about 0.03 moles/100 g support was dissolved in this solution. Puralox (100 g) was then added to this mixture and the excess water removed under reduced pressure using the drying profile in Table 1 to obtain a free flowing powder.

TABLE 1

| Drying profile for impregnated support | | |
|---|---|---|
| Temperature (° C.) | Pressure (mbar) | Time (min) |
| 60 | 250 | 15 |
| 75 | 250 | 30 |
| 85 | 250 | 30 |
| 85 | 250-130 | 120 |
| 85 | 130-50 | 15 |
| 85 | 50 | 180 |

The free flowing powder was then calcined in a fluidised bed calciner with a heating ramp rate of 1° C./min to 250° C. with a hold time of 6 hours, using a GHSV of 2.5 $Nm^3/kgCo(NO_3)_2.6H_2O/hour$.

Then, in a second impregnation stage, the above steps were repeated using $Co(NO_3)_2.6H_2O$ (56.8 g) and $[Pt(NH_4)_4(NO_3)_2]$ (0.042 g) dissolved in water (100 g). The previously calcined material (100 g) was added to this mixture and the excess water removed under reduced pressure using the drying profile in Table 1 to obtain a free flowing powder. The free flowing powder was then again calcined in a fluidised bed calciner with a heating ramp rate of 1° C./min to 250° C. with a hold time of 6 hours, using a GHSV of 2.5 $Nm^3/kgCo(NO_3)_2.6H_2O/hour$.

Example 2 (Comparative)—30 g Co/0.04 g Pt/3.1 g Mn/100 g un-Modified $Al_2O_3$ (Mn as Promoter)

A cobalt based Fischer-Tropsch synthesis catalyst precursor was prepared as described in Example 1.

In this example, manganese was added as a catalyst promoter. After the second impregnation stage, $Mn(NO_3)_2.4H_2O$ (10.1 g) was dissolved in water (100 g) and added to the calcined material (100 g). The excess water was removed under reduced pressure using the drying profile in Table 1 to obtain a free flowing powder. The free flowing powder was then again calcined in a fluidised bed calciner with a heating ramp rate of 1° C./min to 250° C. with a hold time of 6 hours, using a GHSV of 2.5 $Nm^3/kgCo(NO_3)_2.6H_2O/hour$.

Example 3 (Comparative)—Ti—$Al_2O_3$ (Puralox) Support (Ti as Modifier)

Titanium(IV)iso-propoxide (17.2 g) was added to dry ethanol (78.9 g) and allowed to mix for 10 minutes. $Al_2O_3$ (Puralox) (100 g) was added to this solution and allowed to mix for a further 10 minutes. Following this, the ethanol was removed under reduced pressure using the drying profile in Table 2 to obtain a free flowing powder.

TABLE 2

Drying profile for the Ti impregnated Puralox material

| Pressure (mbar) | Temperature (° C.) | Time (min) |
| --- | --- | --- |
| 842 | 60 | 10 |
| 500 | 60 | 30 |
| 400 | 60 | 30 |
| 300 | 60 | 30 |
| 200 | 60 | 60 |
| 100 | 60 | 60 |
| 50 | 60 | 60 |

After the drying step, the modified support was calcined in a fluidized bed calciner with a GHSV of 2.5 Nm$^3$/kg support/hour using air as the calcination gas using a heating rate of 1° C./min to 425° C. with no hold step at this temperature. After this fluidised bed calcination step, the support material was calcined further in a muffle oven to 550° C. at a heating rate of 5° C./min and a final hold time of 5 hours. The resulting modified support included 2.6 g Ti/100 g Al$_2$O$_3$.

Example 4 (Comparative)—Mn—Al$_2$O$_3$ (Puralox) Support (Mn as Modifier)

Manganese(II)acetate tetrahydrate (13.8 g) was dissolved in water (80-100 g) and mixed for 10 minutes. Al$_2$O$_3$ (Puralox) (100 g) was added to this solution and mixed for a further 10 minutes. Following this, the water was removed under reduced pressure using the drying profile in Table 3 to obtain a free flowing powder.

TABLE 3

Drying profile for the Mn impregnated Puralox material

| Pressure (mbar) | Temperature (° C.) | Time (min) |
| --- | --- | --- |
| 100 | 85 | 60 |
| 50 | 85 | 180 |

After the drying step, the modified support was calcined in a fluidized bed calciner with a GHSV of 2.5 Nm$^3$/hour/kg support using air as the calcination gas using a heating rate of 1° C./min to 425° C. with no hold step at this temperature. After this fluidised bed calcination step, the respective support material was calcined further in a muffle oven to 550° C. at a heating rate of 5° C./min and a final hold time of 5 hours. The resulting modified support included 3.1 g Mn/100 g Al$_2$O$_3$.

Example 5 (Comparative)—MnTi—Al$_2$O$_3$ (Puralox) Support (Mn and Ti as Modifiers)

The Ti—Al$_2$O$_3$ support obtained from Example 3, was impregnated with manganese(II)acetate tetrahydrate as described in Example 4. The resulting modified support included 2.6 g Ti/3.1 g Mn/100 g Al$_2$O$_3$.

Example 6 (Comparative)—30 g Co/0.075 g Pt/100 g Ti—Al$_2$O$_3$ (Ti as Modifier)

A cobalt based Fischer-Tropsch synthesis catalyst precursor with the composition 30 g Co/0.075 g Pt/100 g support was prepared as described in Example 1, however, Ti—Al$_2$O$_3$ support as described in Example 3 was used.

Example 7 (Comparative)—30 g Co/0.075 g Pt/100 g Mn—Al$_2$O$_3$ (Mn as Modifier)

A cobalt based Fischer-Tropsch synthesis catalyst precursor with the composition 30 g Co/0.075 g Pt/100 g support was prepared as described in Example 1. However, no maleic acid was added during catalyst preparation. Mn—Al$_2$O$_3$ support as described in Example 4 was used.

Example 8 (Comparative)—30 g Co/0.075 g Pt/100 g MnTi—Al$_2$O$_3$ (Ti and Mn as Modifiers)

A cobalt based Fischer-Tropsch synthesis catalyst precursor with the composition 30 g Co/0.075 g Pt/100 g support was prepared as described in Example 1. However, no maleic acid was added during catalyst preparation. MnTi—Al$_2$O$_3$ support as described in Example 5, was used.

Example 9 (Comparative)—30 g Co/0.075 g Pt/3.1 g Mn/100 g Ti—Al$_2$O$_3$ (Ti as Modifier and Mn as Promoter)

A cobalt based Fischer-Tropsch synthesis catalyst precursor with the composition 30 g Co/0.075 g Pt/3.1 g Mn/100 g support was prepared as described in Example 2, however, Ti—Al$_2$O$_3$ support as described in Example 3, was used.

Example 10 (Comparative)—30 g Co/0.04 g Pt/100 g Si—Al$_2$O$_3$ (Si as Modifier)

A cobalt based Fischer-Tropsch synthesis catalyst precursor with the composition 30 g Co/0.04 g Pt/100 g support was prepared as described in Example 1. However, 2.1 g Si/100 g Al$_2$O$_3$ support was used, using TEOS (tetra ethoxy silane) as starting material for the support modification as described in U.S. Pat. No. 6,638,889.

Example 11 (Comparative)—30 g Co/0.04 g Pt/3.1 g Mn/100 g Si—Al$_2$O$_3$ (Si as Modifier and Mn as Promoter)

A cobalt based Fischer-Tropsch synthesis catalyst precursor was prepared as described in Example 10. However, during the second impregnation stage, Co(NO$_3$)$_2$·6H$_2$O (56.8 g), [Pt(NH$_4$)$_4$(NO$_3$)$_2$] (0.042 g) and Mn(NO$_3$)$_2$·4H$_2$O (11.6 g) was dissolved in water (100 g) and added to the calcined material obtained in the first impregnation stage (100 g).

Example 12 (Comparative)—30 g Co/0.075 g Pt/100 g Ti—Al$_2$O$_3$ (Ti as Modifier)

A cobalt based Fischer-Tropsch synthesis catalyst precursor with the composition 30 g Co/0.075 g Pt/100 g support was prepared as described in Example 1, however, no maleic acid was added during catalyst preparation. Ti—Al$_2$O$_3$ was used and was prepared as described in Example 3.

Example 13 (Comparative)—30 g Co/0.075 g Pt/100 g Ti—Al$_2$O$_3$ (Ti as Modifier)

A cobalt based Fischer-Tropsch synthesis catalyst precursor was prepared as described in Example 12. However, 5 g Ti/00 g Al$_2$O$_3$ support was used and was prepared as described in Example 3.

Example 14 (Comparative)—30 g Co/0.075 g Pt/100 g Ti—Al$_2$O$_3$ (Ti as Modifier)

A cobalt based Fischer-Tropsch synthesis catalyst precursor was prepared as described in Example 12. However, 10 g Ti/100 g Al$_2$O$_3$ support was used and was prepared as described in Example 3.

Example 15—Reduction

The calcined catalyst precursors were reduced prior to Fischer-Tropsch synthesis using pure H$_2$ flowing at 2.0 Nm$^3$/kg Catalyst/hour at atmospheric pressure. The following heating profile was used, 1° C./min to 110° C. hold 3 hours followed with, 1° C./min to 425° C. hold 10 hours. The reduced catalyst was cooled down to room temperature and suspended into molten wax and loaded in a CSTR under an inert gas blanket (argon or nitrogen).

Example 16—Fischer-Tropsch Synthesis

The activated and wax protected catalysts, as described in Example 15, were tested for their slurry phase FTS performance in a laboratory micro slurry CSTR at a reactor temperature of 230° C. and a reactor pressure of about 22 bar during which a pure H$_2$ and CO and Ar feed gas mixture was utilised with a ~5% Ar content and a total feed molar H$_2$/CO ratio of about 1.8. This reactor was electrically heated and sufficiently high stirrer speeds were employed as to eliminate any gas-liquid mass transfer limitations. The feed gas space velocity was changed such that the syngas conversion was around 78±1%. The water partial pressure was about 10 bar.

Discussion

FIG. 1 shows the percentage difference in FT rate for Examples 1, 2, 6-8, 10, 11 and 33 relative to Example 9 and can be calculated as (FT rate of Ex. 1, 2, 6-8, 10, 11 or 33—FT rate of Ex. 9)/FT rate of Ex. 9. As can be seen, Example 2 (Co/3.1 g Mn/100 g un-modified Al$_2$O$_3$) shows that the addition of manganese as catalyst promoter did not improve the activity stability of the catalyst relative to Example 1 (the un-promoted and un-modified catalyst sample), with time on-line. This trend was also observed in comparing catalysts containing the Si-modified Al$_2$O$_3$ support, promoted with manganese as in Example 11 (Co/3.1 g Mn/100 g Si—Al$_2$O$_3$) with Example 10 (Co/100 g Si—Al$_2$O$_3$). Example 9 (Co/3.1 g Mn/100 g Ti—Al$_2$O$_3$) showed initial catalyst deactivation, however, after 5 days on-line the catalyst performance stabilized and remained stable over a 50 day period.

Example 6 (Co/100 g Ti—Al$_2$O$_3$) and Example 7 (Co/100 g Mn—Al$_2$O$_3$) showed that titanium and manganese as Al$_2$O$_3$ support modifiers respectively, resulted in an enhancement in activity and activity stability relative to Example 1, the un-promoted and un-modified catalyst sample.

Turning to Example 7, this Example showed black wax, which is an indication of catalyst break-up. This was not observed for the catalysts containing the combination of titanium and manganese support modifications (Example 8, Co/100 g MnTi—Al$_2$O$_3$).

The catalysts containing the combination of titanium and manganese, either manganese added as support modifier (Example 8) or catalyst promoter (Example 9), showed a significant enhancement in activity and activity stability relative to Examples 1, 2, 6, 7, 10 and 11.

Figure 2:
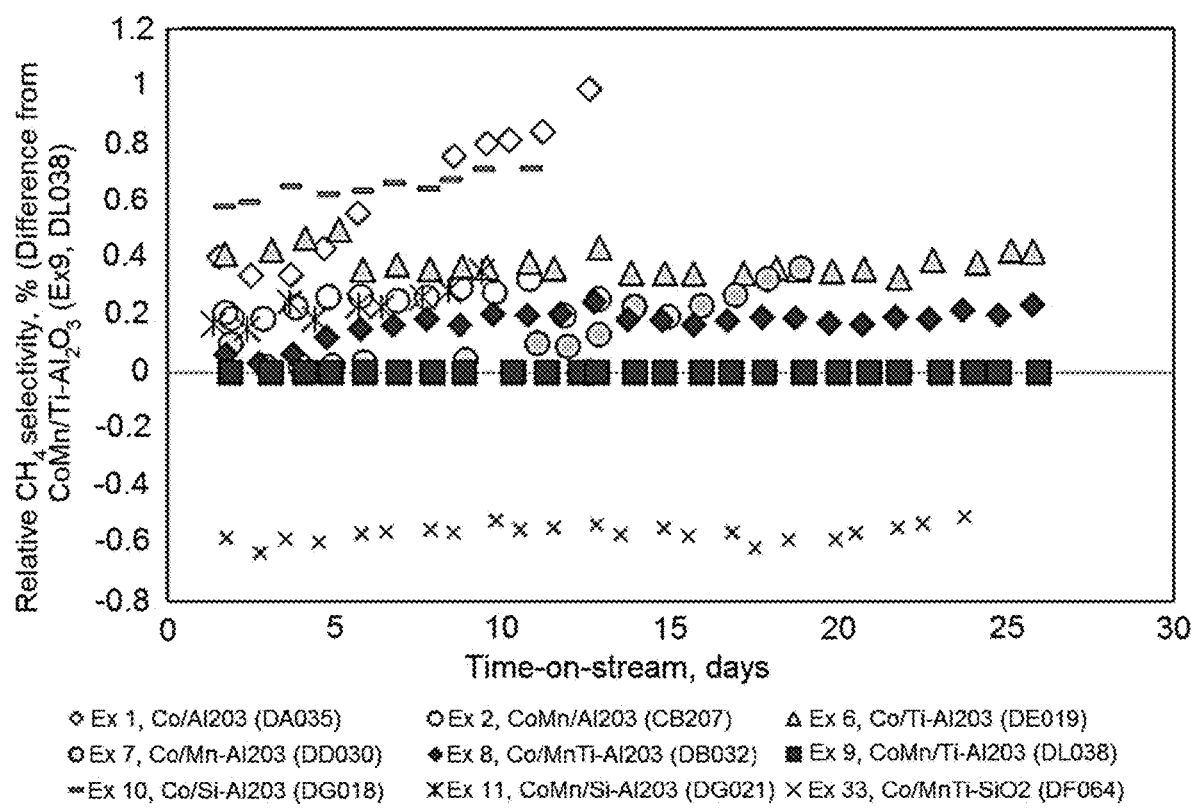
FIG. 2: is a graph showing methane selectivity over Examples 1, 2, 6-8, 10, 11 and 33 relative to Example 9.

The percentage difference in methane selectivity over the Examples 1, 2, 6-8, 10, 11 and 33 relative to Example 9, is shown in FIG. 2 and can be calculate as (% CH$_4$ selectivity of Ex. 1, 2, 6-8, 10, 11 or 33—% CH$_4$ selectivity of Ex. 9)/% CH$_4$ selectivity of Ex. 9. As can be seen, Examples 8 and 9 containing the Mn/Ti combination showed lower and stable methane selectivity over time compared to the rest of the tested catalysts samples. Example 7, containing the Mn-modified Al$_2$O$_3$, showed initial low methane selectivity, which increased to the methane selectivity observed for Example 6, containing the Ti-modified Al$_2$O$_3$ support.

Table 4 below shows the FT performance over Examples 12-14 relative to the initial activities. These samples were prepared using Ti-modified Al$_2$O$_3$ with varying levels of Ti modification. As can be seen, increasing the Ti content from 2.6 g Ti/100 g Al$_2$O$_3$ to 10 g Ti/100 g Al$_2$O$_3$ did not result in a relative improvement in activity stability of the catalysts compared to that of Example 12. The catalysts containing the higher loading Ti resulted in lower activity stability with time on-line.

TABLE 4

| | The relative FT rate[1] over Examples 12-14 tested under conditions as described in Example 16 | | |
|---|---|---|---|
| Time on-stream, days | Example 12, 2.6 g Ti/100 g Al$_2$O$_3$) | Example 13, (5 g Ti—Al$_2$O$_3$) | Example 14, (10 g Ti—Al$_2$O$_3$) |
| 1 | 1 | 1 | 1 |
| 19 | 0.53 | 0.38 | 0.37 |

[1]Relative to the initial FT rate ((CO + CO$_2$) μmol/CO/gs)) and Error is 5% e.g. 1 ± 0.05

Example 17—Fischer-Tropsch Synthesis

The activated and wax protected catalysts, as described in Example 15, for Examples 8 and 9 were tested for their slurry phase FTS performance in a laboratory micro slurry CSTR at a reactor temperature of 230° C. and a reactor pressure of about 19 bar during which a pure H$_2$, CO and Ar feed gas mixture was utilised with a 10% Ar content and a total feed molar H$_2$/CO ratio of ~1.5.

This reactor was electrically heated and sufficiently high stirrer speeds were employed as to eliminate any gas-liquid mass transfer limitations. The feed gas space velocity was changed such that the syngas conversion was around 72±1%. The water partial pressure was about 6 bar.

Examples 8 and 9 were tested under the conditions described in Example 17. As can be seen from Table 5, Example 8, containing the MnTi support modification and Example 9 (containing Mn as promoter and Ti as support modifier) showed comparable relative FT activities and methane selectivities with time on-line, showing the beneficial effect of the combination of MnTi and adding Mn as catalyst promoter or support modifier under the FT conditions.

TABLE 5

FT performance over Examples 8 and 9 with time on-line under conditions as described in Example 17

| Time on-stream, days | Relative FT rate[1] | Relative $CH_4$ selectivty[2] |
|---|---|---|
| Example 8, Co/MnTi—$Al_2O_3$ | | |
| 1 | 1 | 1 |
| 9 | 0.8 | 0.88 |
| 30 | 0.71 | 0.86 |
| Example 9, CoMn/Ti—$Al_2O_3$ | | |
| 1 | 1 | 1 |
| 8 | 0.78 | 0.89 |
| 30 | 0.67 | 0.84 |

[1]Relative to the initial FT rate ((CO + $CO_2$) μmol/CO/gs)) and Error is 5% e.g. 1 ± 0.05
[2]Drift in % $CH_4$ selectivity relative to day 1; C % excluding $CO_2$ formation and Error is 0.3 percentage points, e.g. 5.8 ± 0.3

Example 18 (Comparative)—30 g Co/0.075 g Pt/100 g Mn—$Al_2O_3$

A cobalt based Fischer-Tropsch synthesis catalyst precursor with the composition 30 g Co/0.075 g Pt/100 g support was prepared as described in Example 1. However, no maleic acid was added during catalyst preparation. Mn—$Al_2O_3$ support as described in Example 4 was used. However, the resulting modified support consisted of 2.1 g Mn/100 g $Al_2O_3$.

Example 19 (Comparative)—30 g Co/0.075 g Pt/100 g Mn—$Al_2O_3$

A cobalt based Fischer-Tropsch synthesis catalyst precursor with the composition 30 g Co/0.075 g Pt/100 g support was prepared as described in Example 1. However, no maleic acid was added during catalyst preparation. Mn—$Al_2O_3$ support as described in Example 4 was used. However, the resulting modified support consisted of 7.5 g Mn/100 g $Al_2O_3$.

Example 20 (Comparative)—30 g Co/0.075 g Pt/100 g Mn—$Al_2O_3$

A cobalt based Fischer-Tropsch synthesis catalyst precursor with the composition 30 g Co/0.075 g Pt/100 g support was prepared as described in Example 1. However, no maleic acid was added during catalyst preparation. Mn—$Al_2O_3$ support as described in Example 4 was used. However, the resulting modified support consisted of 10 g Mn/100 g $Al_2O_3$.

Example 21—Fischer-Tropsch Synthesis

The activated and wax protected catalysts, as described in Example 15, for Examples 18-20 were tested for their slurry phase FTS performance in laboratory micro slurry CSTR. The pressure was increased to 18 bar and the temperature to 230° C., where after the synthesis was introduced.

The synthesis feed gas consisted of hydrogen, carbon monoxide and it contained 10% argon as an internal standard with a total feed molar $H_2$/CO ratio of ~1.6. This reactor was electrically heated and sufficiently high stirrer speeds were employed so as to eliminate any gas-liquid mass transfer limitations. The % $H_2$+CO conversion were maintained at 60%±2, by controlling the feed flow by means of Brooks mass flow controllers. The water partial pressure was about 5 bar.

Table 6 shows the relative FT performance over Examples 18-20. These samples were prepared using Mn-modified $Al_2O_3$ with varying levels of Mn modification. No beneficial effect was observed with the increased Mn content from 2.1 g Mn/100 g $Al_2O_3$ to 10 g Mn/100 g $Al_2O_3$. An increase in Mn levels resulted in a significant drift (decrease) in the FT rates with time on-stream.

TABLE 6

The relative FT rate[1] over Examples 18-20 tested under conditions as described in Example 21

| Time on-line, days | Example 18, (2.1 g Mn/100 g $Al_2O_3$) | Example 19, (7.5 g Mn/100 g $Al_2O_3$) | Example 20, (10 g Mn/100 g $Al_2O_3$) |
|---|---|---|---|
| 1 | 1 | 1 | 1 |
| 5 | 0.94 | 0.72 | 0.45 |

[1]Relative to the initial FT rate ((CO + $CO_2$) μmol/CO/gs)) and Error is 5% e.g. 1 ± 0.05

Example 22 (Comparative)—MnSi—$Al_2O_3$ (Puralox) Support

The Si—$Al_2O_3$ support as described in Example 10 was impregnated with manganese(II)acetate tetrahydrate as described in Example 4. The resulting modified support consisted of 3 g Mn/100 g $SiAl_2O_3$.

Example 23 (Comparative)—MnSi—$Al_2O_3$ (Puralox) Support

The Si—$Al_2O_3$ support as described in Example 10 was impregnated with manganese(II)acetate tetrahydrate as described in Example 4. The resulting modified support consisted of 5 g Mn/100 g Si—$Al_2O_3$.

Example 24 (Conductivity Measurements)

Figure 3:
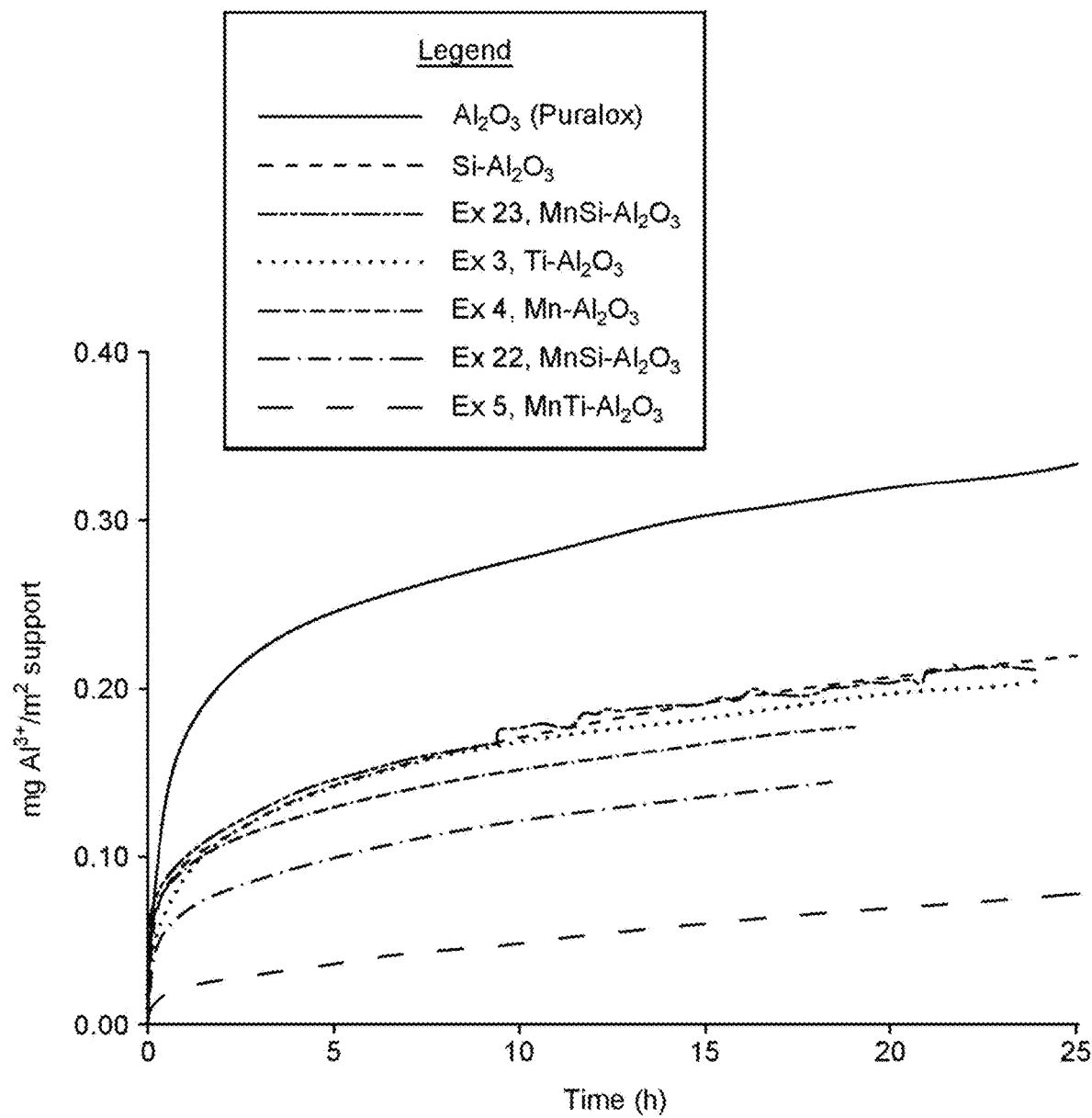
FIG. 3: is a graph depicting cumulative Al dissolution as a function of time for the Mn-modified, Ti-modified, MnTi-modified, unmodified alumina, Si—$Al_2O$ and MnSi—$Al_2O_3$ supports.

Alumina dissolves in an aqueous medium at low pH. The dissolution of alumina results in the formation of aluminium ions. As more and more alumina dissolves, the concentration of aluminium increases with time. An increase in aluminium with time was followed by monitoring the conductivity at a constant pH of 2. The pH was kept constant by automated addition of a 10% nitric acid solution. The results are given in FIG. 3 for the modified and un-modified $Al_2O_3$.

The Ti (Example 3), Mn (Example 4) and Si modified $Al_2O_3$ supports exhibited very similar Al-dissolution behaviour over time. The MnSi modification of the $Al_2O_3$ (Example 22) resulted in a decrease in the Al-dissolution. However, a further increase in the Mn loading (Example 23) negated the suppression of the Al-dissolution and resulted in the Al-dissolution behaviour similar to the Si-modified $Al_2O_3$ support. Surprisingly, it can be seen that over the MnTi-modified support (Example 5) the Al-dissolution was significantly suppressed relative to the MnSi modified $Al_2O_3$ (Example 22).

Example 25 (Comparative)—30 g Co/0.075 g Pt/3.1 g Mn/100 g (2.6 g Ti/100 g $Al_2O_3$) (Co-Hydrolysis, Ti as Modifier and Mn as Promoter), C4639

A cobalt based Fisher-Tropsch synthesis catalyst precursor with the composition 30 g Co/0.075 g Pt/3.1 g Mn/100 g (2.6 g Ti/100 g Al$_2$O$_3$) was prepared as described in Example 9, however the Ti—Al$_2$O$_3$ support used in Example 9 was replaced with a titanium-containing support that was prepared via co-hydrolysis of titanium (IV) 2-ethylhexoxide and Al-hexanolate as described in Example 37 of WO 2014020507.

Example 26 (Comparative)—30 g Co/0.075 g Pt/3.1 g Mn/100 g (2.6 g Ti/100 g Al$_2$O$_3$ (Calcined PURAL 200™ as the Support, Slurry Impregnated Ti as Modifier and Mn as Promoter), C4685

A cobalt based Fisher-Tropsch synthesis catalyst precursor was prepared with the composition 30 g Co/0.075 g Pt/3.1 g Mn/100 g (2.6 g Ti/100 g Al$_2$O$_3$) as described in Example 9, however, the Puralox used in Example 9 was replaced with calcined PURAL 200™ which has a pore diameter similar to the pore diameter of the support of Example 25 and has a surface area of about 90 m$^2$/g.

Example 27—Reduction and Fischer-Tropsch Synthesis (FTS)

The calcined catalyst precursors of Examples 25 and 26 were reduced and suspended into molten wax as described in Example 15. The FTS performance of the activated and wax protected catalysts of Examples 25 and 26 were evaluated in a fix bed reactor at 230° C. and a reactor pressure of about 16 bar utilizing a feed gas mixture with an inlet molar H$_2$/CO ratio of about 1.6. The feed gas space velocity was changed such that the syngas conversion was ~62%-65%.

Discussion

Table 7 shows that similar FTS catalyst performance results were obtained in comparing the Co/Pt/Mn/Ti—Al$_2$O$_3$ catalyst sample prepared via co-hydrolysis of the Ti-modified support (Example 25) with Example 26 (slurry impregnation of Ti), demonstrating that co-hydrolysis of the Ti-modified support is an alternative to slurry impregnation of titanium on alumina.

TABLE 7

FT performance over Examples 25 and 26 under conditions as described in Example 27

CH$_4$ selectivity[1]

| Time on-line, days | Example 25, C4639[2] Co/Pt/Mn/ Ti—Al$_2$O$_3$ with co-hydrolysis | Example 26, C4685[2] Co/Pt/Mn/ Ti—Al$_2$O$_3$ with slurry impregnation | % difference in absolute CH$_4$ selectivity between Ex. 25 and Ex. 26[3] |
|---|---|---|---|
| 1 | 1.00 | 1.00 | 0.06 |
| 2 | 1.00 | 1.02 | 0.03 |
| 3 | 1.01 | 1.01 | 0.07 |
| 7 | 1.05 | | |

| | Relative FT rate[4] | | % difference in absolute FT rates between Ex. 25 and Ex. 26[5] |
|---|---|---|---|
| 1 | 1.00 | 1.00 | 0.14 |
| 2 | 0.97 | 0.97 | 0.15 |
| 3 | 0.93 | 0.94 | 0.13 |
| 7 | 0.88 | | |

[1]C % excluding CO$_2$ formation
[2]Drift in % CH$_4$ selectivity relative to day 1
[3]% CH$_4$ selectivity (sel) difference between Ex. 25 and Ex. 26 = (% CH$_4$ sel of Ex. 25 − % CH$_4$ sel of Ex. 26)/% CH$_4$ sel of Ex. 26
[4]Relative to the initial FT rate ((CO + CO$_2$) μmol/CO/gs))
[5]% difference in FT rates between Ex. 25 and Ex. 26 = (FT rate of Ex. 25 − FT rate of Ex. 26)/FT rate of Ex. 26

Example 28: (Comparative)—30 g Co/0.075 g Pt/5 g Ni/100 g (2.6 g Ti/100 g Al$_2$O$_3$) (Ti as Modifier and Ni as Promoter), C4140

Co(NO$_3$)$_2$.6H$_2$O (11.9 g), (NH$_3$)$_4$Pt(NO$_3$)$_2$ (0.0075 g) and Ni(NO$_3$)$_2$.6H$_2$O (1.9 g) were dissolved in water (13 ml for Co, 2 ml for Pt, 2 ml for Ni). The pH of the solution was adjusted to 2.3 using diluted nitric acid. 15 g of the Ti-modified Puralox support as described in Example 3 was added and the excess water removed under reduced pressure using the drying profile in Table 8 to obtain a free flowing powder.

TABLE 8

Drying profile

| Pressure (mbar) | Temperature (° C.) | Time (min) |
|---|---|---|
| Atmospheric | 60 | 10 |
| 280 | 60 | 30 |
| 280 | 75 | 90 |
| 280 | 85 | 60 |
| 50 | 85 | 60 |
| 50 | 90 | 120 |

20 g of the free flowing sample was calcined in a vertical furnace using an air flow of 1000 ml/min and a heating rate of 1° C./min to 250° C. with a hold time of 6 hours. The above steps were repeated in a second impregnation stage by dissolving Co(NO$_3$)$_2$.6H$_2$O (6.8 g), (NH$_4$)Pt(NO)$_2$ (0.01 g) and Ni(NO$_3$)$_2$.6H$_2$O (1.2 g) in water (9 ml for Co, 2 ml for Pt, 3 ml for Ni). The previously calcined (first impregnation stage) material (12 g) was added to the mixture and the excess water removed under reduced pressure using the drying profile in Table 8. 15 g of the free flowing sample was calcined in a vertical furnace using an air flow of 750 ml/min and a heating rate of 1° C./min to 250° C. with a hold time of 6 hours.

Example 29: (Comparative)—30 g Co/0.075 g Pt/3.1 g Mn/100 g (2.6 g Ti/100 g Al$_2$O$_3$) (Ti as Modifier and Mn as Promoter—Similar to Example 9, but with Smaller Quantities and Different Drying Profile), C4144

Co(NO)$_2$.6H$_2$O (13.3 g) and (NH$_4$)Pt(NO)$_2$ (0.0075 g) were dissolved in water (13 ml for Co, 3 ml for Pt). The pH of the solution was adjusted to 2.3 using diluted nitric acid. 15 g of the Ti-modified Puralox support as described in Example 3 was added and the excess water removed under reduced pressure using the drying profile in Table 9 to obtain a free flowing powder.

TABLE 9

Drying profile

| Pressure (mbar) | Temperature (° C.) | Time (min) |
|---|---|---|
| Atmospheric | 60 | 10 |
| 280 | 60 | 30 |
| 250 | 75 | 30 |
| 250 | 85 | 30 |
| 250-130 | 85 | 120 gradient |
| 130-50 | 85 | 15 gradient |
| 50 | 85 | 180 |

20 g of the free flowing sample was calcined in a vertical furnace using an air flow of 1000 ml/min and a heating rate of 1° C./min to 250° C. with a hold time of 6 hours. In a second impregnation stage, the above steps were repeated using $Co(NO_3)_2 \cdot 6H_2O$ (5.75 g) and $(NH_4)_4Pt(NO)_2$ (0.01 g) as well as $Mn(NO_3)_2 \cdot 4H_2O$ (1.4 g) by dissolving it in water (10 ml for Co, 2 ml for Pt, 3 ml for Mn). 12 g of the first impregnation stage calcined material was added to the mixture and the excess water was removed under reduced pressure using the drying profile of Table 9 to obtain a free flowing powder. 15 g free flowing sample was calcined in a vertical furnace using an air flow of 750 ml/min and a heating rate of 1° C./min to 250° C. with a hold time of 6 hours.

Example 30—Reduction and Fischer-Tropsch Synthesis (FTS)

The calcined catalyst precursors of Examples 28 and 29 were reduced and suspended into molten wax as described in Example 15. The FTS performance of the activated and wax protected catalysts of Examples 28 and 29 were evaluated in a fix bed reactor at 230° C. as described in Example 27.

Discussion

It is known that nickel can be a used as an activity stability promoter [Ind. Eng. Chem. Res. 2010, 49, 4140-4148 and U.S. Pat. No. 8,143,186]. However, the addition of Ni as promoter to the $Co/Pt/Ti-Al_2O_3$ FTS catalyst did not demonstrate the same Co FTS catalyst performance as when Mn was used as promoter. Mn as promoter resulted in lower methane selectivity with higher activity compared to Ni as promoter. Table 10 illustrates the extent of deactivation of the catalysts as described in Example 28 and Example 29 relative to its initial activity as well as the drift in methane selectivity obtained over catalysts as prepared in Example 28 and 29 and activated and tested as described in Example 30 relative to its initial methane selectivity.

TABLE 10

FTS performance over Example 28 (Co/Pt/Ni//Ti—Al$_2$O$_3$) and Example 29 (Co/Pt/Mn/Ti—Al$_2$O$_3$) with time-on-line under conditions as described in Example 30

| | CH$_4$ selectivity[1] | | |
|---|---|---|---|
| Time on-line, days | Example 28, C4140[2] Co/Pt/Ni/ Ti—Al$_2$O$_3$ | Example 29, C4144[2] Co/Pt/Mn/ Ti—Al$_2$O$_3$ | % difference in absolute CH$_4$ selectivity between Ex. 28 and Ex. 29[3] |
| 1 | 1.00 | 1.00 | 0.78 |
| 3 | 0.94 | 1.03 | 0.64 |
| 5 | 0.93 | 1.04 | 0.59 |
| 10 | | 1.04 | |

| Relative FT rate[4] | | % difference in absolute FT rates between Ex. 28 and Ex. 29[5] |
|---|---|---|
| 1 | 1.00 | 1.00 | −0.27 |
| 3 | 1.10 | 0.93 | −0.14 |
| 5 | 1.17 | 0.92 | −0.08 |
| 10 | | 0.88 | |

[1] C % excluding CO$_2$ formation
[2] Drift in % CH$_4$ selectivity relative to day 1
[3] % CH$_4$ selectivity (sel) difference between Ex. 28 and Ex. 29 = (% CH$_4$ sel of Ex. 28 − % CH$_4$ sel of Ex. 29)/% CH$_4$ sel of Ex. 29
[4] Relative to the initial FT rate ((CO + CO$_2$) μmol/CO/gs))
[5] % difference in FT rates between Ex. 28 and Ex. 29 = (FT rate of Ex. 28 − FT rate of Ex. 29)/FT rate of Ex. 29

Example 31: (Comparative)—30 g Co/0.075 g Pt/3.1 g Mn/100 g (2.6 g Ti/100 g Al$_2$O$_3$) with Ti as Modifier and Mn as Promoter Using a Hydrothermal Deposition Method (HDM), C4585

$Co(NO_3)_2 \cdot 6H_2O$ (37.2 g), $(NH_3)_4Pt(NO_3)_2$ (0.07 g), $Mn(NO_3)_2 \cdot 4H_2O$ (7.06 g) and maleic acid (1.25 g) were dissolved in 75 ml water. Cobalt hydroxide (3 g) was added to the nitrate solution where after 50 g of the Ti-modified Puralox support as described in Example 3 was added. An additional 3 g of $Co(OH)_2$ was added to the slurry and mixed at 95° C. in a rotary evaporator at 65 rpm. Additional 3 g of $Co(OH)_2$ was added until the desired loading of 11.8 g was reached. The mixture was stirred until complete absorption of $Co(OH)_2$ (for approximately 3 hours). The excess water was removed under reduced pressure using the drying profile of Table 11 to obtain a free flowing powder and calcined at 250° C. at a heating rate of 1° C./min in air (2500 ml/min/gcat) for 6 hours.

TABLE 11

| Drying profile | | |
|---|---|---|
| Pressure (mbar) | Temperature (° C.) | Time (min) |
| 500-130 | 95 | 180 |
| 50 | 100 | 120 |

The calcined catalyst precursor was reduced and suspended into molten wax as described in Example 15. The catalyst was tested for its slurry phase FTS performance in a laboratory micro slurry CSTR as described in Example 17.

As can be seen from Table 12, Example 31, prepared using HDM, showed lower methane selectivity and higher activity when comparing to the absolute CH$_4$ selectivity and reaction rates of Example 9 (the cobalt nitrate slurry impregnation method). The drift in methane selectivity of Example 31 is slightly more than Example 9, but the deactivation relative today 1 over time on stream of Example 31 and Example 9 are comparable.

TABLE 12

FTS performance over Example 31 (Co/Pt/Mn/Ti—Al$_2$O$_3$ - prepared using HDM) with time-on-line under conditions as described in Example 17)

| | CH$_4$ selectivity[1] | | |
|---|---|---|---|
| Time on-line, days | Example 31, C4585[2] Co/Pt/Mn/ Ti—Al$_2$O$_3$ (HDM) | Example 9, C2155[2] Co/Pt/Mn/ Ti—Al$_2$O$_3$ | % difference in absolute CH$_4$ selectivity between Ex. 31 and Ex. 9[3] |
| 1 | 1.00 | 1.00 | −0.15 |
| 17 | 0.85 | 0.89 | −0.19 |
| 31 | 0.76 | 0.86 | −0.26 |

TABLE 12-continued

FTS performance over Example 31 (Co/Pt/Mn/Ti—Al$_2$O$_3$ - prepared using HDM) with time-on-line under conditions as described in Example 17)

| | Relative FT rate[4] | | % difference in absolute FT rates between Ex. 31 and Ex. 9[5] |
|---|---|---|---|
| 1 | 1.00 | 1.00 | 0.21 |
| 17 | 0.66 | 0.70 | 0.15 |
| 31 | 0.66 | 0.70 | 0.15 |

[1]C % excluding CO$_2$ formation
[2]Drift in % CH$_4$ selectivity relative to day 1
[3]% CH$_4$ selectivity (sel) difference between C4585 and C2155 = (% CH$_4$ sel of C4585 − % CH$_4$ sel of C2155)/% CH$_4$ sel of C2155
[4]Relative to the initial FT rate ((CO + CO$_2$) μmol/CO/gs))
[5]% difference in FT rates between C4585 and C2155 = (FT rate of C4585 − FT rate of C2155)/FT rate of C2155

Example 32: (Comparative)—MnTi—SiO$_2$ (Mn and Ti as Support Modifiers on a Silica Support)—(FSQ-15)

Titanium (IV)iso-propoxide (17.2 g) was added to dry ethanol (78.9 g) and allowed to mix for 10 minutes. Amorphous, preshaped silica-gel (100 g), CARiACT Q-15 (an average pore diameter of 15 nm), as obtained from Fuji Silysia Chemical LTD, was added to this solution and allowed to mix for a further 10 minutes. The ethanol was removed under reduced pressure using the drying profile in Table 2 to obtain a free flowing powder.

Manganese(II)acetate tetrahydrate (13.8 g Mn(Ac)$_2$.4H$_2$O for 3.1 g Mn loading) was dissolved in water (80-100 g) and allowed to mix for 10 minutes. The free flowing powder obtained from the Ti(OPr)$_4$ modified silica (100 g) was added to this solution and allowed to mix for a further 10 minutes. The water was removed under reduced pressure using the drying profile in Table 3 to obtain a free flowing powder. After the drying step, the modified support was calcined in a fluidised bed with a GHSV of 2.5 Nm$^3$/kg support/hour using air as calcination gas at a heating rate of 1° C./min to 425° C. The support material was further calcined in a muffle oven to 500-550° C. at a heating rate of 5° C./min and a final hold time of hours. The resulting modified support included 3.1 g Mn/2.6 g Ti/100 g SiO$_2$.

Example 33: (Comparative)—30 g Co/0.075 g Pt/100 g (3.1 g Mn/2.6 g Ti/100 g SiO$_2$) (Mn and Ti as Support Modifiers), (FSQ-15), C4859

In a first impregnation step, Co(NO$_3$)$_2$.6H$_2$O (39.5 g) and (NH$_4$)$_3$Pt(NO$_3$)$_2$ (0.025 g) were dissolved in water (50 g). The pH of the solution was adjusted to 2.3 using diluted nitric acid. The MnTi—SiO$_2$ (50 g) support as described in Example 32 was added to the mixture and the excess water removed under reduced pressure using the drying profile in Table 1 to obtain a free flowing powder. The free flowing powder was calcined in a fluidized bed calciner with a heating ramp rate of 1° C./min to 250° C. with a hold time of 6 hours using a GHSV of 2.5 Nm$^3$/kg(Co(NO$_3$)$_2$.6H$_2$O)/hour.

In a second impregnation step, Co(NO$_3$)$_2$.6H$_2$O (28.4 g) and (NH$_4$)$_3$Pt(NO$_3$)$_2$ (0.04 g) were dissolved in water (50 g). The pH of the solution was adjusted to 2.3 using diluted nitric acid. The calcined material of the first impregnation step (50 g) was then added to this mixture and the excess water was removed under reduced pressure using the drying profile in Table 1 to obtain a free flowing powder. The free flowing powder was calcined in a fluidized bed calciner with a heating ramp rate of 1° C./min to 250° C. with a hold time of 6 hours using a GHSV of 2.5 Nm$^3$/kg(Co(NO$_3$)$_2$.6H$_2$O)/hour.

The calcined catalyst material was reduced and suspended into molten wax as described in Example 15. The catalyst was tested for its slurry phase FTS performance in a laboratory micro slurry CSTR as described in Example 17.

Discussion

As mentioned before, FIG. 1 shows the difference in FT rate for Examples 1, 2, 6-8, 10, 11 and 33 relative to Example 9. The Mn/Ti combination on a silica support (Example 33) also demonstrated a significant enhancement in activity compared to the comparative examples that do not comprise of the Mn/Ti combination.

As mentioned before, FIG. 2 shows the difference in percentage methane selectivity for Examples 1, 2, 6-8, 10, 11 and 33 relative to Example 9. Example 33 containing the Mn/Ti combination on a silica support showed the lowest methane selectivity over time compared to the rest of the tested catalysts samples.

Example 34: (Comparative)—MnTi—SiO$_2$ (FSQ-6)

A modified support with the composition 3.1 g Mn/2.6 g Ti/100 g SiO$_2$ was prepared as described in Example 32, however, the support was replaced with CARiACT Q-6 with an average pore diameter of 6 nm.

Example 35: (Comparative)—MnTi—SiO$_2$ (FSQ-30)

A modified support with the composition 3.1 g Mn/2.6 g Ti/100 g SiO$_2$ was prepared as described in Example 32, however, the support was replaced with CARiACT Q-30 with an average pore diameter of 30 nm.

Example 36: (Comparative)—MnTi—SiO$_2$ (FSQ-50)

A modified support with the composition 3.1 g Mn/2.6 g Ti/100 g SiO$_2$ was prepared as described in Example 32, however, the support was replaced with CARiACT Q-50 with an average pore diameter of 50 nm.

Example 37: (Comparative)—30 g Co/0.075 g Pt/100 g MnTi—SiO$_2$ (FSQ-6), C4881

A cobalt based Fischer-Tropsch synthesis catalyst precursor with the composition 30 g Co/0.075 g Pt/100 g support was prepared as described in Example 33, however, MnTi—SiO$_2$ (FSQ-6) support as described in Example 34 was used.

Example 38: (Inventive)—30 g Co/0.075 g Pt/100 g MnTi—SiO$_2$ (FSQ-30), C4812

A cobalt based Fischer-Tropsch synthesis catalyst precursor with the composition 30 g Co/0.075 g Pt/100 g support was prepared as described in Example 33, however, MnTi—SiO$_2$ (FSQ-30) support as described in Example 35 was used.

Example 39: (Comparative)—30 g Co/0.075 g Pt/100 g MnTi—SiO$_2$ (FSQ-50), C4860

A cobalt based Fischer-Tropsch synthesis catalyst precursor with the composition 30 g Co/0.075 g Pt/100 g support was prepared as described in Example 33, however, MnTi—SiO$_2$ (FSQ-50) support as described in Example 36 was used.

Example 40: (Inventive)—30 g Co/0.075 g Pt/2.5 g MAc/100 g MnTi—SiO$_2$ (FSQ-30), C4987

A cobalt based Fischer-Tropsch synthesis catalyst precursor with the composition 30 g Co/0.075 g Pt/100 g MnTi—SiO$_2$ (FSQ-30) support was prepared as described in Example 38, however, maleic acid (MAc) (1.25 g) was added to the solution during the first impregnation step.

Example 41: (Comparative)—30 g Co/0.075 g Pt/100 g SiO$_2$ (FSQ-30), C4408 (Unmodified SiO$_2$ A cobalt based Fischer-Tropsch synthesis catalyst precursor with the composition 30 g Co/0.075 g Pt/100 g support was prepared as follows using FSQ-30 as support.

Co(NO$_3$)$_2$.6H$_2$O (11.8 g) and (NH$_4$)$_3$Pt(NO$_3$)$_2$ (0.0075 g) were dissolved in distilled water (15 ml for Co, 2 ml for Pt). FSQ-30 silica (15 g) was added to this mixture and the excess water removed under reduced pressure using the drying profile in Table 13 to obtain a free flowing powder.

TABLE 13

| Drying profile | | |
| --- | --- | --- |
| Temperature (° C.) | Pressure (mbar) | Time (min) |
| 60 | No Vacuum | 10 |
| 60 | 280 | 30 |
| 75 | 280 | 90 |
| 85 | 280 | 60 |
| 85 | 50 | 180 |

17 g of the free flowing sample was calcined in a vertical furnace using an air flow of 700 ml/min (GHSV=2.500 Nm$^3$/kgCo(NO$_3$)$_2$.6H$_2$O/hour) and a heating rate of 1° C./min to 250° C. with a hold time of 6 hours.

The above steps were repeated in a second impregnation stage by dissolving Co(NO$_3$)$_2$.6H$_2$O (6.8 g) and (NH$_3$)$_4$Pt(NO$_3$)$_2$ (0.0098 g) in water (12 ml for Co, 2 ml for Pt). The previously calcined (first impregnation stage) material (12 g) was added to the mixture and the excess water removed under reduced pressure using the drying profile in Table 13. 15 g of the free flowing sample was calcined in a vertical furnace using an air flow of 680 ml/min (GHSV=2.700 Nm$^3$/kgCo(NO$_3$)$_2$.6H$_2$O/hour) and a heating rate of 1° C./min to 250° C. with a hold time of 6 hours.

Example 42 (Comparative)—30 g Co/0.075 g Pt/3.1 g Mn/100 g SiO$_2$ (FSQ-30), C4404, (Mn as Promoter)

Co(NO$_3$)$_2$.6H$_2$O (9.4 g), (NH$_4$)$_3$Pt(NO$_3$)$_2$ (0.006 g) and Mn(NO$_3$)$_2$.4H$_2$O (1.7 g) were dissolved in distilled water (10 ml for Co, 1 ml for Pt and 2 ml for Mn). Unmodified FSQ-30 silica (12 g) was added to this mixture and the excess water removed under reduced pressure using the drying profile in Table 13 to obtain a free flowing powder. 15 g of the free flowing sample was calcined in a vertical furnace using an air flow of 620 ml/min (GHSV=2.500 Nm$^3$/kgCo(NO$_3$)$_2$.6H$_2$O/hour) and a heating rate of 1° C./min to 250° C. with a hold time of 6 hours.

The above steps were repeated in a second impregnation stage by dissolving Co(NO$_3$)$_2$.6H$_2$O (5.7 g) and (NH$_3$)$_4$Pt(NO$_3$)$_2$ (0.0081 g) in water (10 ml for Co, 1 ml for Pt). The previously calcined (first impregnation stage) material (10 g) was added to the mixture and the excess water removed under reduced pressure using the drying profile in Table 13. 11 g of the free flowing sample was calcined in a vertical furnace using an air flow of 500 ml/min (GHSV=2.700 Nm$^3$/kgCo(NO$_3$)$_2$.6H$_2$O/hour) and a heating rate of 1° C./min to 250° C. with a hold time of 6 hours.

Example 43 (Comparative)—3.1 g Mn/100 g SiO$_2$ (FSQ-30) (Mn as Support Modifier)

A manganese modified support was prepared as described in Example 4, however, silica (FSQ-30) (100 g) was used as support. The resulting modified support included 3.1 g Mn/100 g SiO$_2$.

Example 44 (Comparative)—30 g Co/0.075 g Pt/2.5 g MAc/100 g Mn—SiO$_2$ (FSQ-30), C4998 (Mn as Support Modifier and MAc)

A cobalt based Fischer-Tropsch synthesis catalyst precursor with the composition 30 g Co/0.075 g Pt/2.5 g MAc/100 g support was prepared as described in Example 40, however, Mn—SiO$_2$ (50 g) modified support as described in Example 43 was used.

Example 45 (Comparative)—2.6 g Ti/100 g SiO$_2$ (FSQ-30), (Ti as Support Modifier)

A titanium modified support was prepared as described in Example 3, however, FSQ-30 silica (100 g) was used as support. The resulting modified support included 2.6 g Ti/100 g SiO$_2$.

Example 46 (Comparative)—30 g Co/0.075 g Pt/100 g Ti—SiO$_2$ (FSQ-30), C4410

Co(NO$_3$)$_2$.6H$_2$O (11.8 g) and (NH$_4$)$_3$Pt(NO$_3$)$_2$ (0.0075 g) were dissolved in water (15 ml for Co, 2 ml for Pt). The Ti—SiO$_2$ (15 g) support as described in Example 45 was added to the mixture and the excess water removed under reduced pressure using the drying profile in Table 13 to obtain a free flowing powder. 17 g of the free flowing sample was calcined in a vertical furnace using an air flow of 700 ml/min (GHSV=2.500 Nm$^3$/kgCo(NO$_3$)$_2$.6H$_2$O/hour) and a heating rate of 1° C./min to 250° C. with a hold time of 6 hours.

The above steps were repeated in a second impregnation stage by dissolving Co(NO$_3$)$_2$.6H$_2$O (6.8 g) and (NH$_3$)$_4$Pt(NO$_3$)$_2$ (0.0098 g) in water (12 ml for Co, 2 ml for Pt). The previously calcined (first impregnation stage) material (12 g) was added to the mixture and the excess water removed under reduced pressure using the drying profile in Table 13. 15 g of the free flowing sample was calcined in a vertical furnace using an air flow of 680 ml/min (GHSV=2.700 Nm$^3$/kgCo(NO$_3$)$_2$.6H$_2$O/hour) and a heating rate of 1° C./min to 250° C. with a hold time of 6 hours.

Example 47 (Comparative)—30 g Co/0.075 g Pt/2.5 g MAc/100 g Ti—SiO$_2$ (FSQ-30), C4997

A cobalt based Fischer-Tropsch synthesis catalyst precursor with the composition 30 g Co/0.075 g Pt/2.5 g MAc/100 g support was prepared as described in Example 40, however, the Ti-modified silica support as described in Example 45 was used.

Example 48 (Inventive)—30 g Co/0.075 g Pt/2.5 g MAc/3.1 g Mn/100 g Ti—SiO$_2$ (FSQ-30), C4991 (Mn as Promoter in First Impregnation)

A cobalt based Fischer-Tropsch synthesis catalyst precursor with the composition 30 g Co/0.075 g Pt/2.5 MAc/100 g Ti—SiO$_2$ (FSQ-30) was prepared as described in Example 47, however, in this example manganese was added as a catalyst promoter in the first impregnation stage prior to pH adjustment by means of dissolving Mn(NO$_3$)$_2$.4H$_2$O (7.1 g) in water (100 g).

Example 49 (Inventive)—30 g Co/0.075 g Pt/2.5 g MAc/3.1 g Mn/100 g Ti—SiO$_2$ (FSQ-30), C4990 (Mn as Promoter in Second Impregnation)

A cobalt based Fischer-Tropsch synthesis catalyst precursor with the composition 30 g Co/0.075 g Pt/2.5 MAc/100 g Ti—SiO$_2$ (FSQ-30) was prepared as described in Example 47, however, in this example manganese was added as a catalyst promoter in the second impregnation stage prior to pH adjustment by means of dissolving Mn(NO$_3$)$_2$.4H$_2$O (7.1 g) in water (100 g).

Example 50 (Inventive)—30 g Co/0.075 g Pt/3.1 g Mn/100 g Ti—SiO$_2$ (FSQ-30), C4996 (Mn as Promoter in First Impregnation)

A cobalt based Fischer-Tropsch synthesis catalyst precursor was prepared as described in Example 48, however, in this example no maleic acid was added during the catalyst preparation.

Example 51—Standard Reduction (SR)

The silica supported calcined catalyst materials in Examples 33, 37-42, 44 and 46-50 were reduced in situ prior to Fischer-Tropsch synthesis using pure H$_2$ flowing at 2.0 Nm$^3$/kg catalyst/hour at atmospheric pressure. The temperature was ramped at 1° C./min to 385° C.-425° C. and maintained for 6 hours.

Example 52—Reduction—Carbiding—Reduction Activation (RCR)

The silica supported calcined catalyst materials in Examples 33 and 37-39 were activated in situ prior to Fischer-Tropsch synthesis in a fixed bed reactor by means of the following procedure:
  Increasing the temperature to 380° C. at 1° C./min in hydrogen (4 500 ml/gcat/h) under atmospheric pressure and maintain for 6 hours, followed by cooling down to 200° C. in hydrogen.
  Replacing hydrogen with argon (2 000 ml/gcat/h) and hold for 20 minutes.
  In the carbide formation step, replace argon with CO (6 000 ml/gcat/h) and start increasing the temperature to 230° C. at 1° C./min and maintain for 6 hours at 6 bar CO.
  Whilst cooling under CO (1 000 ml/gcat/h) from 230 to 170° C. the pressure is dropped to atmospheric pressure.
  At 170° C. and atmospheric pressure, the CO was replaced with argon (20 min; 2 000 ml/gcat/h) where after the argon was again replaced by hydrogen.
  In an activation step, increasing the temperature to 425° C. under hydrogen (8 000 ml/gcat/h) at 1° C./min and at a hold time of 7 hours, followed by cooling down to 200° C. in hydrogen after which FTS was started.

Example 53—Fischer-Tropsch Synthesis

The FTS performance of the activated silica supported catalysts of Examples 33, 37-42, 44 and 46-50 were evaluated in a fix bed reactor at 230° C. and 17 bar pressure. The inlet H$_2$/CO ratio was ~1.6. The feed gas space velocity was changed as such to control the syngas conversion at roughly 50%-55%.

Discussion

Pore Diameter: Standard Reduction (SR)

Figure 4:
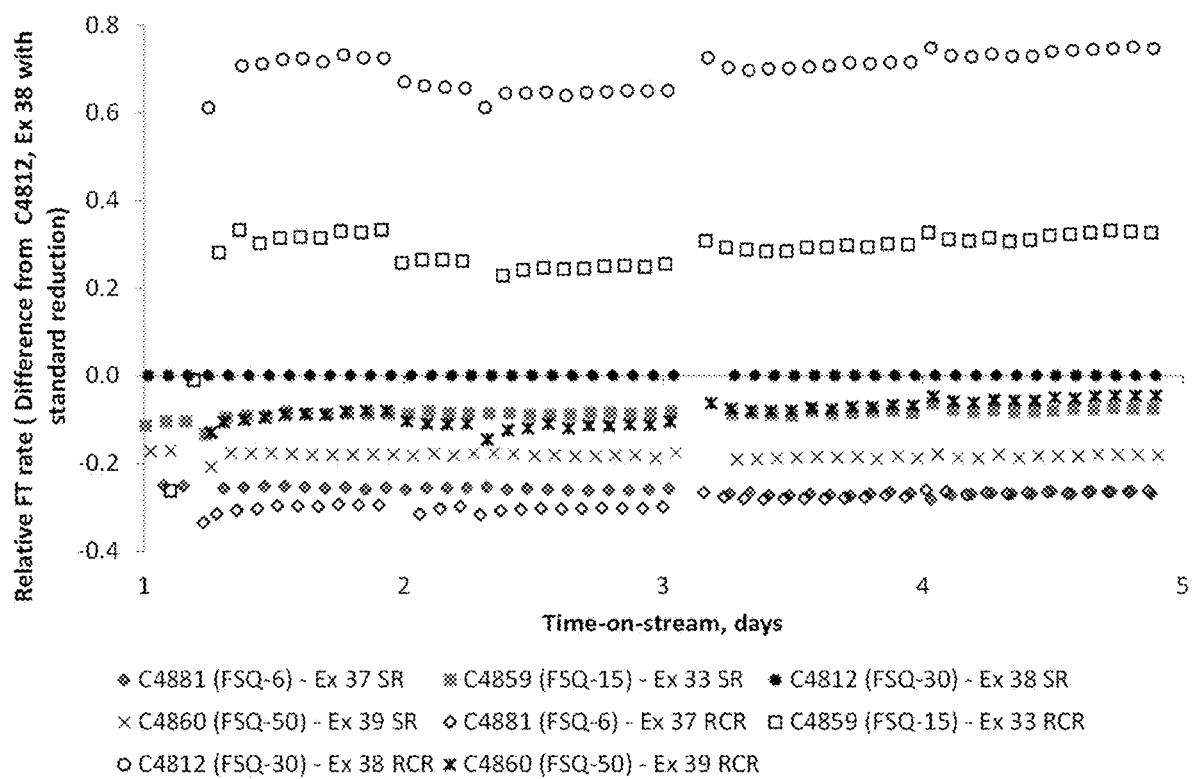
FIG. 4: is a graph showing the FT rate over Examples 33, 37, 38 RCR and 39 relative to Example 38 SR.
Figure 5:
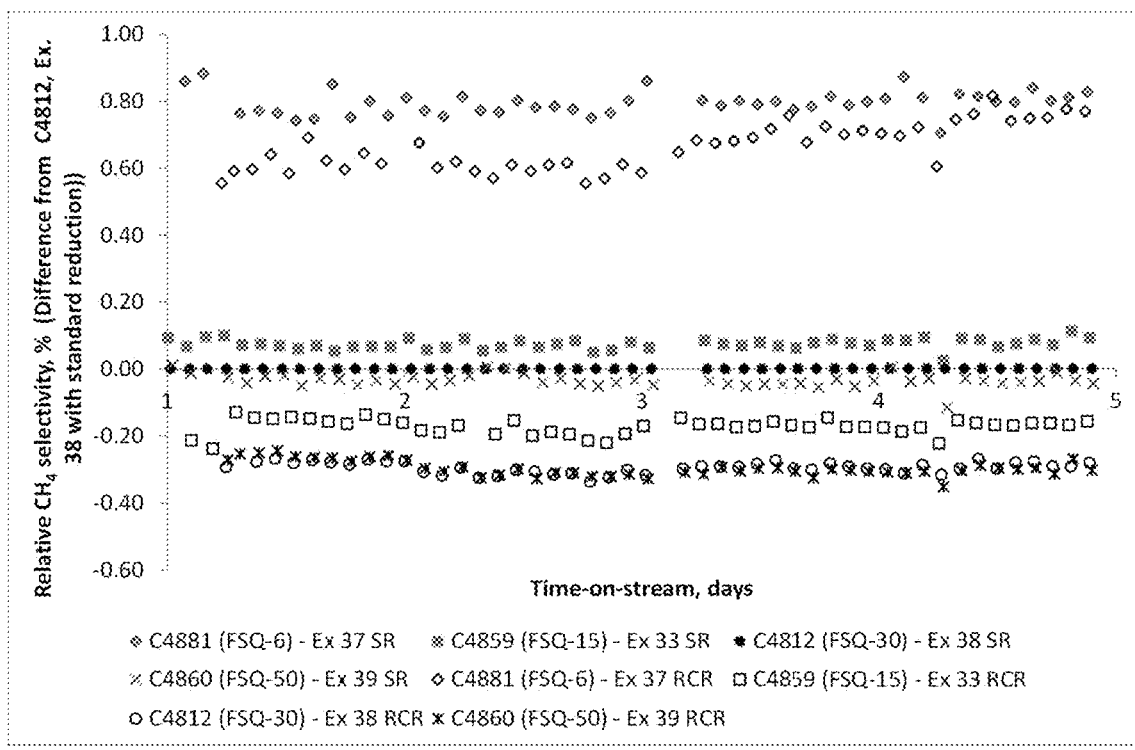
FIG. 5: is a graph showing the $CH_4$ selectivity over Examples 33, 37, 38 RCR and 39 relative to Example 38 SR.

FIG. 4 and FIG. 5 show the difference in FT rates and percentage CH$_4$ selectivity of Example 33 (FSQ-15), Example 37 (FSQ-6) and Example 39 (FSQ-50) relative to Example 38 (FSQ-30) (activated at 385° C. with standard reduction as described in Example 51).

Figure 6:
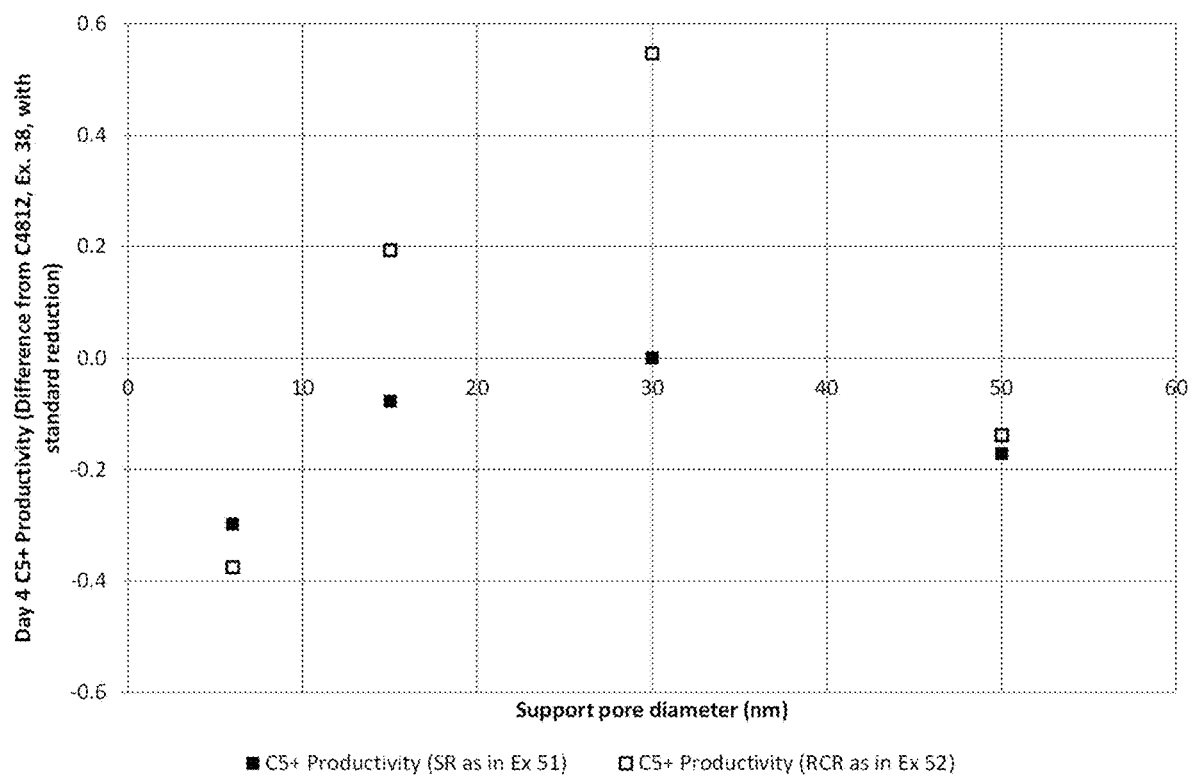
FIG. 6: is a graph showing C5+ productivity over Example 38 SR.

Example 38 with an average pore diameter of 30 nm, following standard reduction, demonstrated the highest FT rates when compared to the other catalysts following standard reduction. The catalysts with the larger average support pore diameters of 30 nm and 50 nm had the lowest CH$_4$ selectivity, however, from FIG. 6 it can be seen that the best FTS activity/C5+ selectivity combination (C5+ productivity) is obtained over the Fischer-Tropsch catalyst as described in Example 38 (FSQ-30). The C5+ productivity of the Fischer-Tropsch catalyst as described in Example 37 (FSQ-6) and Example 39 (FSQ-50) was much lower (see FIG. 6).

As mentioned herein before, the C5+ productivity is the unit mass of C5+ hydrocarbons per unit catalyst per unit time and is a function of the rate of CO converted and the C5+ hydrocarbon selectivity of the catalyst.

Pore Diameter: RCR Activation

FIG. 4 and FIG. 5 show the difference in FT rates and percentage CH$_4$ selectivity of Example 33 (FSQ-15), Example 37 (FSQ-6) and Example 39 (FSQ-50) relative to Example 38 (FSQ-30) (activated at 385° C. with standard reduction as described in Example 51).

RCR activation of the silica supported catalysts improved the activities and selectivity of the catalysts further. The RCR activated Fischer-Tropsch catalyst demonstrated an even bigger differentiation in the C5+ productivity for the catalyst as described in Example 38 with a support pore diameter of 30 nm (see FIG. 6).

Maleic Acid (MAc) Addition

The CH$_4$ selectivity obtained over the catalyst where maleic acid was added during the first impregnation step as described in Example 40 (30 g Co/0.075 g Pt/2.5 g MAc/100 g MnTi—SiO$_2$ (FSQ-30)) was comparable with the catalyst CH$_4$ selectivity of the catalyst as described in Example 38 on similar support pore diameters (FSQ-30) (see Table 14). However, the activity and activity stability of the catalyst as described in Example 40 was higher and may be as a result of improved metal dispersion with the maleic acid addition.

TABLE 14

Difference in FTS performance between Example 38 and Example 40 (similar support pore diameter) following standard reduction under conditions as described in Example 50.

Relative CH$_4$ selectivity, %[1]

| Time on-line, days | Example 40, C4987[2] Co/Pt/MAc/ MnTi—SiO$_2$ | Example 38, C4812[2] Co/Pt/ MnTi—SiO$_2$ | Difference in CH$_4$ selectivity of Ex. 40 relative to Ex. 38 [3] |
|---|---|---|---|
| 1 | 1.00 | 1.00 | −0.13 |
| 2 | 0.97 | 0.90 | −0.05 |
| 3 | 0.99 | 0.91 | −0.05 |
| 4 | 1.00 | 0.87 | 0.00 |
| 5 | 1.01 | 0.85 | 0.04 |

Relative FT rate[4]

| Time on-line, days | Example 40, C4987 Co/Pt/MAc/ MnTi—SiO$_2$ | Example 38, C4812 Co/Pt/ MnTi—SiO$_2$ | difference in FT rate of Ex. 40 relative to Ex. 38 [5] |
|---|---|---|---|
| 1 | 1.00 | 1.00 | −0.09 |
| 2 | 0.97 | 0.86 | 0.02 |
| 3 | 0.96 | 0.85 | 0.03 |
| 4 | 0.95 | 0.80 | 0.09 |
| 5 | 0.95 | 0.79 | 0.09 |

[1] C % excluding CO$_2$ formation
[2] Drift in % CH$_4$ selectivity relative to day 1
[3] % CH$_4$ sel difference between Ex. 40 & Ex. 38 = (% CH$_4$ sel of Ex. 40 − % CH$_4$ sel of Ex. 38)/% CH$_4$ sel of Ex. 38
[4] Relative to the initial FT rate ((CO + CO$_2$) μmol/CO/gs))
[5] Difference in FT rates between Ex. 40 & Ex. 38 = ((FT rate of Ex. 40 − FT rate of Ex. 38)/FT rate of Ex. 38)

MnTi—SiO$_2$ Support

Figure 7:
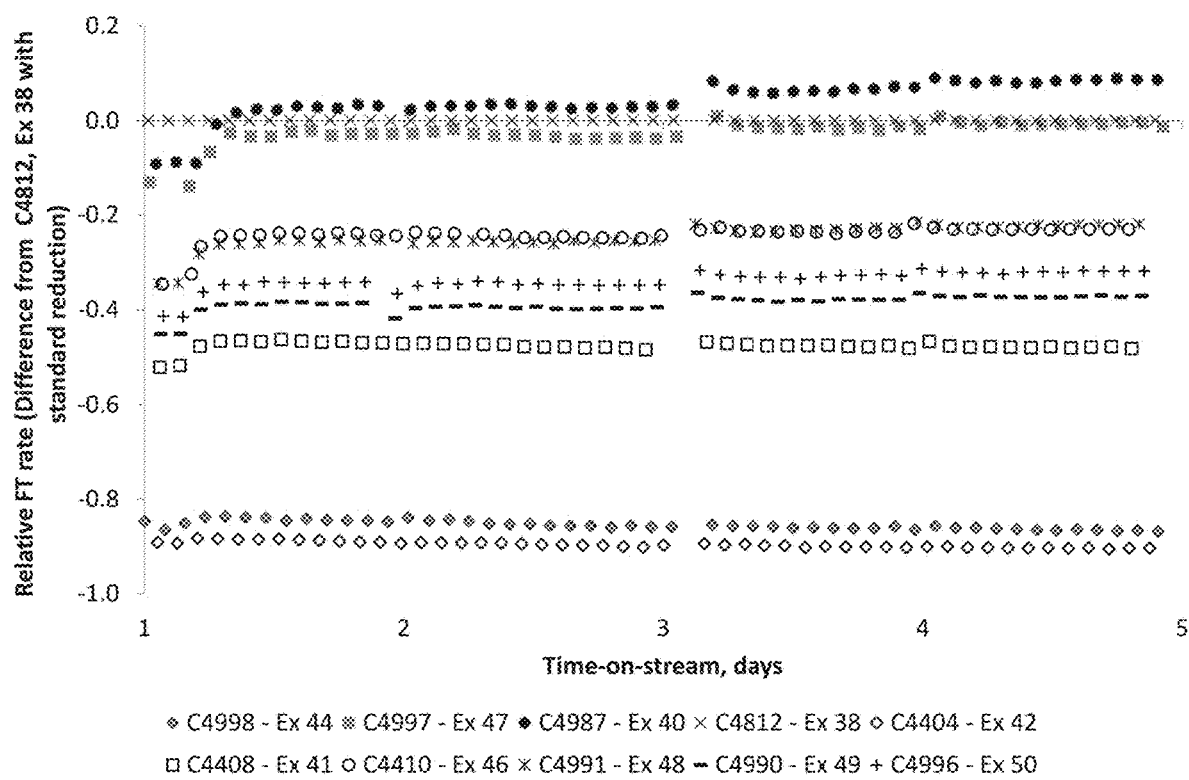
FIG. 7: is a graph showing the FT rate over Examples 40, 41, 42, 44, 46, 47, 48, 49 and 50 relative to Examples 38 SR.
Figure 8:
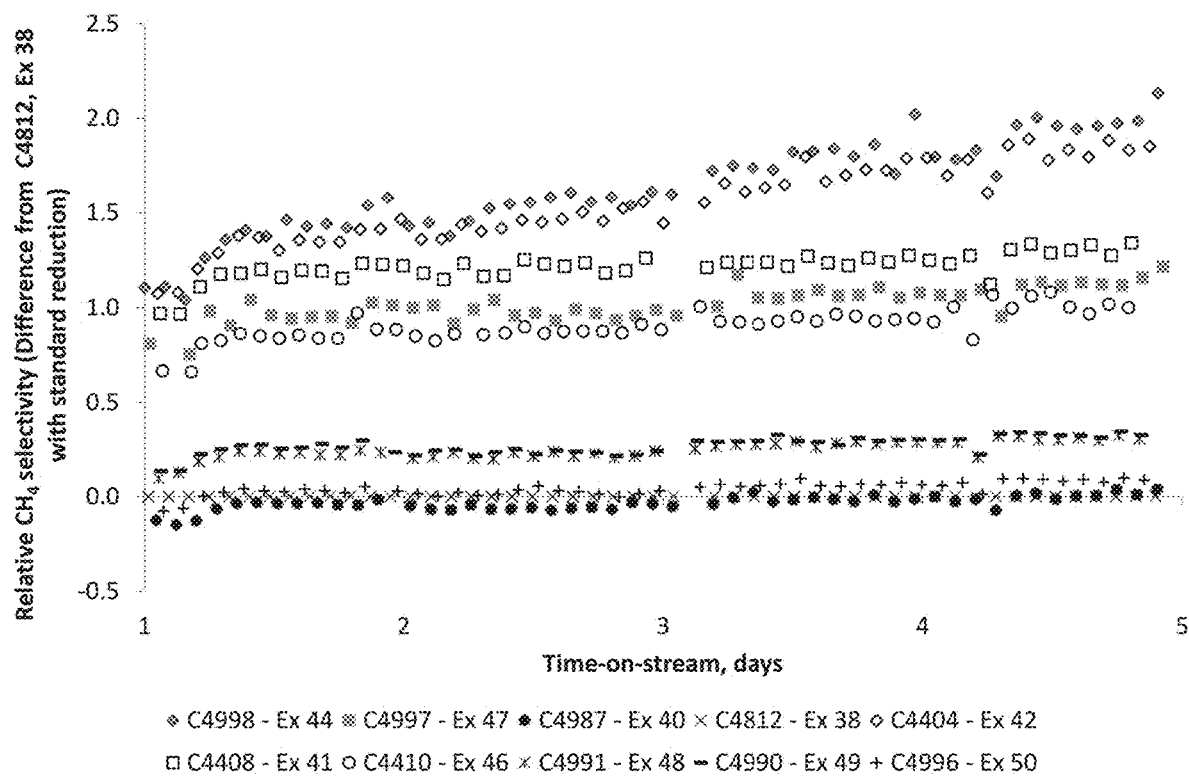
FIG. 8: is a graph showing the $CH_4$ selectivity over Examples 40, 41, 42, 44, 46, 47, 48, 49 and 50 relative to Examples 38 SR.

The combination of Ti and Mn is crucial for high Fischer-Tropsch activity and low CH$_4$ selectivity (see FIG. 7 and FIG. 8). Modification of the silica support with Mn only (Example 44) or as a promoter (Example 42) resulted in a catalyst with lower Fischer-Tropsch performance compared to an unmodified silica support (Example 41). The use of Ti as a support modifier (Example 46 and Example 47 (with MAc)) for the Co Fischer-Tropsch catalyst demonstrated higher Fischer-Tropsch rates relative to the unmodified support (Example 41). However, the CH$_4$ selectivity was not significantly improved when using Ti as a support modifier when compared to an unmodified silica support. When using Ti as a support modifier in combination with Mn (either as support modifier as in Example 38 and Example 40 (with MAc) or as a promoter as in Examples 48, 49 and 50) the CH$_4$ selectivity obtained over these catalysts are the lowest. The use of Mn as a support modifier (Example 38 and Example 40 (with MAc)) resulted in higher FT rates compared to the use of Mn as a promoter (Examples 48, 49 and 50).

Example 54—Attrition Resistance

The attrition resistance of the MnTi—SiO$_2$ (FSQ-30) catalyst support as described in Example was compared to the unmodified FSQ-30 support to determine the physical strength of the modified catalyst support.

A Silverson Homogenizer was used to perform the shear attrition test. Catalyst support (5 g) as described in Example 35 was added to 170 ml distilled water and stirred for 15 minutes at a stirrer speed of 1000 rpm at 25° C. After completion of the shear attrition test the entire sample/mixture was decanted and the PSD (particle size distribution) was measured with a Saturn Digisizer, which is essentially a volume-based technique used to determine the PSD before and after shear testing.

Discussion

The mechanical strength of the modified support as described in Example 35 is shown in Table 15. Mechanical attrition testing indicated that Ti/Mn modified silica is mechanically robust when compared to the unmodified silica with the same pore diameter of 30 nm. The Ti and Mn modifiers therefore improved the mechanical integrity to withstand fracturing of the particles.

TABLE 15

PSD before and after shear testing indicating relative change in volume based mean for Ti/Mn modified silica compared to the unmodified analogue.

|  | Unmodified silica (30 nm pore diameter) | Ti/Mn modified silica (30 nm pore diameter) |
|---|---|---|
| Shear Δ mean | 16.3 | 0.3 |

Example 55—Slurry Phase Fischer-Tropsch Synthesis in NH$_3$ Poison Gas

The Fischer-Tropsch catalyst performance of the catalyst as described in Example 40 (30 g Co/0.075 g Pt/2.5 g MAc/100 g MnTi—SiO$_2$ (FSQ-30)) was tested in a N-contaminated poison gas environment.

The calcined catalyst precursor was reduced at conditions as described in Example 51, cooled down to room temperature, suspended into molten wax and loaded in a CSTR under an inert gas blanket (argon or nitrogen).

The catalysts as described in Example 40 were tested for its slurry phase FTS performance in a laboratory micro slurry CSTR at a reactor temperature of 230° C. and a reactor pressure of about 17 bar and a total feed molar H$_2$/CO ratio of about 1.63. The reactor was electrically heated and sufficiently high stirrer speeds were employed as to eliminate any gas-liquid mass transfer limitations. The feed gas space velocity was changed such that the syngas conversion was around 63%. The water partial pressure was less than 5 bar. The syngas feed contained 2000 vppb NH$_3$.

Example 56—Slurry Phase Fischer-Tropsch Synthesis in NH$_3$ Poison Gas (RCR Activation)

The catalyst as described in Example 40 was tested for its slurry phase FTS performance in a laboratory micro slurry CSTR at similar conditions as described in Example 55. However, the catalyst was activated as described in Example 52.

Example 57—Slurry Phase Fischer-Tropsch Synthesis in HCN Poison Gas

The catalyst as described in Example 40 was tested for its slurry phase FTS performance in a laboratory micro slurry CSTR at similar conditions as described in Example 55. However, the syngas feed contained about 2000 vppb HCN instead of 2000 vppb NH$_3$.

Discussion

The FT rate and CH$_4$ selectivity relative to the initial (day 3) FT rate and CH$_4$ selectivity obtained over the catalyst as prepared in Example 40 under conditions as described in Example 55-57 are shown in Table 16.

TABLE 16

FT performance over Examples 40 with time on-line under conditions as described in Examples 55-57.

Relative $CH_4$ selectivity[1]

| Time on-line, days | Example 55, $NH_3$, SR | Example 56, $NH_3$, RCR | Example 56, HCN, SR |
|---|---|---|---|
| 3 | 1.00 | 1.00 | 1.00 |
| 12 | 0.99 | 1.05 | 1.04 |
| 23 | 0.99 | 1.00 | 1.06 |
| 32 | 0.81 | 0.91 | 1.07 |

Relative FT rate[2]

| Time on-line, days | Example 55, $NH_3$, SR | Example 56, $NH_3$, RCR | Example 56, HCN, SR |
|---|---|---|---|
| 3 | 1.00 | 1.00 | 1.00 |
| 12 | 0.89 | 1.08 | 0.89 |
| 23 | 0.77 | 0.95 | 0.87 |
| 32 | 0.82 | 0.96 | 0.83 |

[1]Drift in % $CH_4$ selectivity relative to initial (day 3); C % excluding $CO_2$ formation
[2]Relative to the initial (day 3) FT rate ((CO + $CO_2$) mol/CO/gs))

It can be concluded from Table 16 that the Co/Pt/MnTi—$SiO_2$ (FSQ-30) catalyst also performed well under N-contaminated syngas conditions with no significant drift in the $CH_4$ selectivity and no significant drift in the FT rates over time-on-line.

The invention claimed is:

1. A cobalt-containing catalyst composition comprising cobalt and/or a cobalt compound supported on and/or in a silica ($SiO_2$) catalyst support wherein the average pore diameter of the catalyst support is more than 20 nm but less than 50 nm as determined by means of Barrett-Joyner-Halenda (BJH) nitrogen physisorption analysis; the catalyst composition also including a titanium compound on and/or in the catalyst support, and a manganese compound on and/or in the catalyst support,
   wherein the composition includes more than 1 wt % and not more than 10 wt % Ti, based on the weight of the silica ($SiO_2$) catalyst support (excluding the weight of the Ti and Mn), the Ti being present in the form of one or more titanium compounds and
   wherein the composition includes more than 0.5 wt % and less than 10 wt % Mn, based on the weight of the silica ($SiO_2$) catalyst support (excluding the weight of the Ti and Mn), the Mn being present in the form of one or more manganese compounds.

2. The catalyst composition according to claim 1, wherein the silica catalyst support is an amorphous silica support.

3. The catalyst composition according to claim 1, wherein the silica catalyst support has an average pore diameter of more than 22 nm.

4. The catalyst composition according to claim 3, wherein the silica catalyst support has an average pore diameter of from 25 to 35 nm.

5. The catalyst composition according to claim 1, wherein the titanium compound is an organic titanium compound.

6. The catalyst composition according to claim 5, wherein the organic titanium compound is selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato) dihydroxide.

7. The catalyst composition according to claim 1, wherein the manganese compound is an organic manganese compound.

8. The catalyst composition according to claim 1, wherein the manganese compound is an inorganic manganese compound.

9. The catalyst composition according to claim 1, wherein the catalyst composition includes cobalt with a zero valency.

10. A hydrocarbon synthesis process which comprises
    contacting a cobalt-containing catalyst composition of claim 9, with hydrogen and carbon monoxide at a temperature above 100° C. and at a pressure of at least 10 bar with the catalyst, to produce hydrocarbons and optionally, oxygenates of hydrocarbons.

11. The hydrocarbon synthesis process according to claim 10, wherein a hydroprocessing step is included for converting the hydrocarbons and optionally oxygenates thereof to liquid fuels and/or other chemicals.

12. A process for preparing a cobalt-containing catalyst precursor, the process comprising
    introducing a cobalt compound onto and/or into a silica catalyst support wherein the average pore diameter of the catalyst support is more than 20 nm but less than 50 nm as determined by means of Barrett-Joyner-Halenda (BJH) nitrogen physisorption analysis;
    prior to and/or during and/or subsequent to introducing the cobalt compound onto and/or into the catalyst support, introducing a titanium compound onto and/or into the catalyst support in an amount more than 1 wt % and not more than 10 wt % Ti, based on the weight of the silica ($SiO_2$) catalyst support (excluding the weight of the Ti and Mn), the Ti being present in the form of one or more titanium compounds; and
    prior to, and/or during, and/or subsequent to introducing the cobalt compound onto and/or into the catalyst support, introducing a manganese compound onto and/or into the catalyst support in an amount more than 0.5 wt % and less than 10 wt % Mn, based on the weight of the silica ($SiO_2$) catalyst support (excluding the weight of the Ti and Mn), the Mn being present in the form of one or more manganese compounds, thereby providing a cobalt-containing catalyst precursor.

13. A process for preparing a cobalt-containing catalyst, the process comprising
    preparing a cobalt-containing catalyst precursor according to the process of claim 12; and
    reducing the catalyst precursor, thereby activating the catalyst precursor.

* * * * *